US010081795B2

(12) United States Patent
Brown et al.

(10) Patent No.: US 10,081,795 B2
(45) Date of Patent: Sep. 25, 2018

(54) FLAVIVIRUS HOST RANGE MUTATIONS AND USES THEREOF

(75) Inventors: Dennis T. Brown, Raleigh, NC (US); Raquel Hernandez, Raleigh, NC (US); Malcolm E. Thomas, Raleigh, NC (US); Katherine M. Smith, Raleigh, NC (US)

(73) Assignees: Research Development Foundation, Carson City, NV (US); Arbovax, Inc., Raleigh, NC (US)

( * ) Notice: Subject to any disclaimer, the term of this patent is extended or adjusted under 35 U.S.C. 154(b) by 1398 days.

(21) Appl. No.: 13/069,905

(22) Filed: Mar. 23, 2011

(65) Prior Publication Data

US 2011/0236421 A1   Sep. 29, 2011

Related U.S. Application Data

(60) Provisional application No. 61/317,103, filed on Mar. 24, 2010, provisional application No. 61/393,151, filed on Oct. 14, 2010.

(51) Int. Cl.

| | | |
|---|---|---|
| A61K 39/12 | (2006.01) | |
| A61K 39/00 | (2006.01) | |
| C07K 14/005 | (2006.01) | |
| C12N 7/00 | (2006.01) | |
| C07K 16/10 | (2006.01) | |

(52) U.S. Cl.
CPC ............... *C12N 7/00* (2013.01); *A61K 39/12* (2013.01); *C12N 2770/24134* (2013.01); *C12N 2770/24161* (2013.01); *C12N 2770/24162* (2013.01); *Y02A 50/386* (2018.01); *Y02A 50/388* (2018.01); *Y02A 50/39* (2018.01); *Y02A 50/394* (2018.01); *Y02A 50/396* (2018.01)

(58) Field of Classification Search
USPC ........................................................ 424/218
See application file for complete search history.

(56) References Cited

U.S. PATENT DOCUMENTS

| | | | |
|---|---|---|---|
| 6,306,401 B1 | 10/2001 | Brown et al. ............... | 424/218.1 |
| 6,589,533 B1 | 7/2003 | Brown et al. ............... | 424/205.1 |
| 7,128,915 B2 | 10/2006 | Hernandez et al. ........ | 424/199.1 |
| 7,335,363 B2 | 2/2008 | Hernandez et al. ........ | 424/199.1 |
| 7,459,160 B2 | 12/2008 | Monath et al. ............. | 424/199.1 |
| 2002/0106379 A1* | 8/2002 | Hernandez et al. ........ | 424/188.1 |
| 2004/0009469 A1 | 1/2004 | Apt et al. ................... | 435/5 |
| 2005/0053624 A1 | 3/2005 | Arroyo et al. .............. | 424/218.1 |
| 2007/0087354 A1 | 4/2007 | Charneau et al. .......... | 435/6 |
| 2007/0269458 A1 | 11/2007 | Guirakhoo et al. ........ | 424/218.1 |
| 2008/0026004 A1* | 1/2008 | Hernandez et al. ........ A61K 2039/525 |
| 2009/0117149 A1 | 5/2009 | Wicker et al. .............. | 424/199.1 |

FOREIGN PATENT DOCUMENTS

| | | | |
|---|---|---|---|
| WO | WO 2001-038499 | | 5/2001 |
| WO | WO 2009/114207 | | 6/2009 |
| WO | WO2009114207 | * | 9/2009 |
| WO | WO 2012/003320 | | 1/2012 |

OTHER PUBLICATIONS

Hsieh et al., The length of and Nonhydrophobic residues in the transmembrane Domain of Dengue Virus Envelope Protein are Critical for Its Retention and Assembly in the Endoplasmic Reticulum, Apr. 2010. Journal of Virology, 84(9): pp. 4782-4797.*
Tan et al., Characterization of the Dengue Virus Envelope Glycoprotein Expressed in Pichia pastoris, 2007, Methods in Molecular Biology, 379:163-176.*
Liu et al., Recombinant dengue virus-like particles from Pichia pastoris: efficient production and immunological properties, 2009 Epub, Virus Genes, 40:53-59.*
Mukhopadhya et al., "A structural perspective of the flavivirus life cycle", 2005, Nature Reviews, 3:13-22.*
Dengue hemorrhagic fever: Diagnosis, treatment, prevention and control. $2^{nd}$ Edition. World Health Organization 1997. Printed in England.
Adams and Rose, "Structural requirements of a membrane-spanning domain for protein anchoring and cell surface transport," *Cell*, 41(3):1007-1015, 1985.
Allison et al., "Mutational evidence for an internal fusion peptide in flavivirus envelope protein E," *Journal of Virology*, 75(9):4268-4275, 2001.
Bowers et al., "Replication and tissue tropism of the alphavirus Sindbis in the mosquito *Aedes albopictus*," *Virology*, 212(1):1-12, 1995.
Bretscher and Munro, "Cholesterol and the Golgi apparatus," *Science*, 261:1280-1, 1993.
Brown and Condreay, "Replication of the alphaviruses in mosquito cells," In: *The Togaviruses and Flavivirlia*. Schlesinger et al. (Eds.), 11(2/3):171-207, Plenum Press, NY, 1986.
Ceruso and Weinstein, "Structural mimicry of prolin kinks: tertiary packing interactions support local structural distortions," *J. Mol. Biol.*, 318(5):1237-1249, 2002.
Condreay and Brown, "Exclusion of superinfecting homologous virus by Sindbis virus-infected *Aedes albopictus* (mosquito) cells," *J. Virol.*, 58:81-6, 1986.
Eckels et al., "Modification of dengue virus strains by passage in primary dog kidney cells: preparation of candidate vaccines and immunization of monkeys," *Am. J. Trop. Med. Hyg.*, 69:12-16, 2003.

(Continued)

*Primary Examiner* — Barry A Chestnut
(74) *Attorney, Agent, or Firm* — Parker Highlander PLLC

(57) ABSTRACT

Methods and compositions concerning mutant flaviviruses with host range mutations. In some embodiments the invention concerns nucleotide sequences that encode mutant flavivirus proteins. Viruses comprising these sequences that display reduced replication in mammalian cells are provided. In further aspects of the invention, flavivirus vaccine compositions are provided. In another embodiment the invention provides methods for vaccination against flavivirus infection.

24 Claims, 12 Drawing Sheets
Specification includes a Sequence Listing.

(56) References Cited

OTHER PUBLICATIONS

Hernandez et al., "A single deletion in the membrane-proximal region of the Sindbis virus glycoprotein E2 endodomain blocks virus assembly," *J. Virol.*, 74:4220-8, 2000.

Hernandez et al., "Deletions in the transmembrane domain of a sindbis virus glycoprotein alter virus infectivity, stability, and host range," *J. Virol.*, 77(23):12710-12719, 2003.

Hernandez et al., "Sindbis virus: propagation, quantification, and storage," *Curr. Protoc. Microbiol.*, 15:15B-1, 2005.

Li et al., "The flavivirus precursor membrane-envelope protein complex: structure and maturation," *Science*, 319:1830-1834, 2008.

Lobigs and Lee, "Inefficient signalase cleavage promotes efficient nucleocapsid incorporation into budding flavivirus membranes," *J. Virol.*, 78:178-86, 2004.

Lobigs et al., "Evidence that a mechanism for efficient flavivirus budding upregulates MHC class I," *Immunol. Cell Biol.*, 82:184-8, 2004.

Martin et al., "Viremia and antibody response in green monkeys (*Chlorocebus aethiops sabaeus*) infected with dengue virus type 2: a potential model for vaccine testing," *Microbiol. Immunol.*, 53:216-223, 2009.

Martin et al., "Viremia and the magnitude of the immune response upon infection of green monkeys with dengue virus type 2 are strain-dependent," *Curr. Microbiol.*, 59:579-583, 2009.

Mathews et al., "Expanded sequence dependence of thermodynamic parameters improves prediction of RNA secondary structure," *J. Mol. Biol.*, 288:911-40, 1999.

Mitsuhashi et al., "Sterol-free eukaryotic cells from continuous cell lines of insects," *Cell Biol. Int. Rep.*, 7(12):1057-62, 1983.

Monath, "Pathobiology of the flaviviruses," In: *The Togaviridae and Flaviviridae*, Schlesinger et al. (Eds.), 375-440, Plenum Press, NY, 1986.

Mukhopadhyay et al., "A structural perspective of the flavivirus life cycle," *Nat. Rev. Microbiol.*, 3:13-22, 2005.

Murray et al., "Architects of assembly: roles of Flaviviridae non-structural proteins in virion morphogenesis," *Nat. Rev. Micro.*, 6:699-708, 2008.

PCT International Search Report and Written Opinion issued in International application No. PCT/US2011/042600, dated Mar. 21, 2012.

PCT International Search Report and Written Opinion issued in International application No. PCT/US2011/029598, dated Dec. 19, 2011.

Rice et al., "Characterization of serum resistance of Neisseria gonorrhoeae that disseminate. Roles of blocking antibody and gonococcal outer membrane proteins," *J. Clin. Invest.*, 70(1):157-67, 1982.

Samsa et al., "Dengue virus capsid protein usurps lipid droplets for viral particle formation," *PLoS Pathog.*, 5:e1000632, 2009.

Schlesinger and, Schlesinger, "Replication of Togaviruses and Flaviviruses," In: *Virology*, $2^{nd}$ Ed., Fields et al. (Ed.), Raven Press, NY, pp. 697-712, 1990.

Von Heijne, "Proline kinks in transmembrane alpha-helices," *J. Mol. Biol.*, 218(3):499-503, 1991.

West et al., "Mutations in the endodomain of Sindbis virus glycoprotein E2 define sequences critical for virus assembly," *J. Virol.*, 80:4458-68, 2006.

Whitehead et al., "Prospects for a dengue virus vaccine," *Nature*, 5:518-528, 2007.

Zhang et al., "Visualization of membrane protein domains by cryo-electron microscopy of dengue virus," *Nature Structural Biology*, 10(11):907-912, 2003.

Zhang et al., "Susceptibility of the Sf9 insect cell line to infection with adventitious viruses," *Biologicals*, 22:205-13, 1994.

Bryant et al., "Glycosylation of the dengue 2 virus E protein at N67 is critical for virus growth in vtro but not for growth in intrathoracically inoculated *Aedes aegypti* mosquitoes," *Virology*, 366:415-423, 2007.
Nilsson et al., "Proline-induced disruption of a transmembrane $\alpha$-helix in its natural environment," *J. Mol. Biol.*, 284:1165-1175, 1998.
Office Action issued in U.S. Appl. No. 13/173,895, dated Jan. 18, 2013.
Office Action issued in U.S. Appl. No. 13/173,895, dated Oct. 2, 2012.
Maxfield et al., "Cholesterol, the central lipid of mammalian cells," *Curr Opin Cell Biol.*, 22(4):422-429, 2010.
Office Action issued in Indian Application No. 8187/DELNP/2012, dated Jan. 30, 2018.
Office Action issued in European Application No. 11760135.1, dated Oct. 12, 2016.
Smith et al., "Structural mutants of dengue virus 2 transmembrane domains exhibit host-range phenotype," *Virology*, 8:289, 2011.
Smith et al., "Testing of novel dengue virus 2 vaccines in African green monkeys: safety, immunogenicity, and efficacy," *Am. J. Trop. Med. Hyg.*, 87(4):743-753, 2012.

* cited by examiner

FLAVIVIRUS HOST RANGE MUTATIONS AND USES THEREOF

PRIORITY CLAIM

This application claims priority to U.S. Application No. 61/317,103, filed Mar. 24, 2010 and U.S. Application Ser. No. 61/393,151 filed on Oct. 14, 2010, the entire contents of which are hereby incorporated by reference.

BACKGROUND OF THE INVENTION

1. Field of the Invention

The present invention relates generally to virology and disease control. Specifically, the present invention relates to mutated arthropod vectored viruses and their uses as vaccines. In particular aspects, the present invention relates to improved flavivirus constructs for use in preparing vaccines.

2. Description of Related Art

Arthropod vectored viruses (Arboviruses) are viral agents which are transmitted in nature by blood sucking insects. Arboviruses include members of the Alpha-, Flavi- and Bunyaviridae. The family of flaviviruses includes approximately 60 enveloped, positive strand RNA viruses, most of which are transmitted by an insect vector. Many members of this family cause significant public health problems in different regions of the world (Monath, 1986). The genome of all flaviviruses sequenced thus far has the same gene order: 5'-C-preM-E-NS1-NS2A-NS2B-NS3-NS4A-NS4B-N55-3' in which the first three genes code for the structural proteins the capsid (C), the pre-membrane protein (preM) and the envelope protein (E).

By their very nature, flaviviruses, like other Arboviruses, must be able to replicate in the tissues of both the invertebrate insect and the mammalian host (Brown and Condreay, 1986, Bowers et al., 1995). Differences in the genetic and biochemical environment of these two host cell systems provide a basis for the production of host range mutant viruses which can replicate in one host but not the other.

Dengue virus is a positive-sense RNA virus belonging to the Flavivirus genus of the family Flaviviridae. Dengue virus is widely distributed throughout the tropical and semitropical regions of the world and is transmitted to humans by mosquito vectors. Dengue virus is a leading cause of hospitalization and death in children in at least eight tropical Asian countries (WHO, 1997). Currently, Dengue Fever and other flaviviruses are in resurgence in the United States. The U.S. Army and other government agencies have been trying to make vaccines against these viruses since the 1960's with little success. Thus, there is a need to develop flavivirus vaccines for humans.

SUMMARY OF THE INVENTION

Viruses that are transmitted in nature by blood sucking insects are a major source of disease in man and domestic animals. Many of these viruses have lipid membrane bilayers with associated integral membrane proteins as part of their three dimensional structure. These viruses are hybrid structures in which the proteins are provided by the genetic information of the virus and the membrane is the product of the host cell in which the virus is grown. Differences in the composition of the membranes of the mammalian and insect host are exploited in aspects of the present invention to produce virus mutants containing deletions in the membrane spanning domains of the virus membrane proteins. Some of the mutants are capable of replicating and assembling normally in the insect host cell but assemble poorly in the mammalian host cell. These host range mutants could produce immunity to wild-type virus infection when used as a vaccine and represent a novel strategy for the production of vaccines against arthropod vectored, membrane containing viruses like flaviviruses.

In certain aspects of the invention, there is provided an engineered nucleic acid comprising a sequence encoding a modified viral transmembrane protein comprising a mutation, wherein the mutation inhibits the production or infectivity of a virus comprising the modified viral transmembrane protein in mammalian cells. The term nucleic acid sequence as used herein comprises both RNA and DNA sequences, consistent with its usage in the art. The modified transmembrane protein may be able to span or correctly integrate into the membrane of insect cells but not that of mammalian cells due to mutation of one or more amino acids in the viral transmembrane protein, in particular, a transmembrane domain thereof. The virus comprising the modified viral transmembrane protein may be capable of infecting and producing progeny virus in insect cells. The virus also may or may not be capable of infecting; however, the virus may have reduced ability to produce progeny in mammalian cells.

Thus, in accordance with the present invention, the mutation will preferably reside in a transmembrane protein of a flavivirus, for example, the envelope (E) protein of a flavivirus, particularly the E protein's transmembrane domain, and more particularly, the N-terminal transmembrane domain (E-T1 domain).

A linear sequence of a transmembrane domain has a central amino acid defined as that amino acid residue that resides essentially at the center of the membrane spanning amino acids. Thus, in the case of the flavivirus E-T1 domain, the central amino acid will most often be the amino acid closest to the center of the 16 amino acid transmembrane domain, i.e., the $8^{th}$ or $9^{th}$ amino acid used here refers to the central amino acid, which is Glycine (Gly or G) in most of the more common Flaviviruses (see, e.g., Table 1). Such flavivirus E-T1 transmembrane domains include predicted transmembrane domains based on primary sequences.

Alignment of representative Flaviviruses from each of the main groups which are main human pathogens are shown in Table 1. The alignment of the representative Flaviviruses as compared to Dengue virus serotype 2 (DV2) was performed by DNASTAR Lasergene software, MegAlign program, using the Clustal W method. The E-T1 domain in Dengue virus serotype 2 (DV2) served as the basis for E-T1 sequence alignment is predicted as amino acids 452 to 467 of the E protein (Zhang et al., 2003). Other flavivirus E-T1 sequences not shown herein can be determined by optimal sequence alignment to the E-T1 sequences of any of the representative Flaviviruses, for example, by the Bestfit method, and the "central" amino acid determined accordingly.

TABLE 1

Flavivirus E-T1 Sequences (bold: central amino acid)

| Flavivirus | Genome sequence (Genbank #) | E-T1 SEQUENCE | SEQ ID NO: |
|---|---|---|---|
| Dengue 2 Virus | U87411 | $_{452}$SWTMKILIGVIITWIG$_{467}$ | 1 |
| Aroa Virus | AY632536 | $_{458}$SWLSRLMIGALCLWIG$_{473}$ | 2 |
| Bagaza Virus | AY632545 | $_{458}$SWITQGLLGALLLWMG$_{473}$ | 3 |
| Entebbe Bat Virus | DQ837641 | $_{446}$NWIVKILIGTIFLWLG$_{461}$ | 4 |
| Japanese Encephalitis Virus | M18370 | $_{457}$SWITQGLMGALLLWMG$_{472}$ | 5 |
| Modoc Virus | AJ242984 | $_{440}$GFMMKMIISLVLIWFC$_{455}$ | 6 |
| Murry Valley Encephalitis Virus | AF161266 | $_{458}$SWISPGLLGALLLWMG$_{473}$ | 7 |
| Omsk Hemorrhagic Fever Virus | AY193805 | $_{453}$GFLPRILLGISLAWLG$_{468}$ | 8 |
| Rio Bravo Virus | AF144692 | $_{442}$GFLGKLMISGVLIWLC$_{457}$ | 9 |
| St. Louis Encephalitis Virus | DQ525916 | $_{458}$SWITQGLLGALLLWMG$_{473}$ | 10 |
| Tick-borne Encephalitis Virus | U27495 | $_{453}$GFLPKLLLGVALAWLG$_{468}$ | 11 |
| West Nile Virus | DQ211652 | $_{457}$SWITQGLLGALLLWMG$_{472}$ | 12 |
| Yellow Fever Virus | X03700 | $_{451}$NWITKVIMGAVLIWVG$_{466}$ | 13 |
| Zika Virus | AY632535 | $_{457}$SWFSQILIGTLLVWLG$_{472}$ | 14 |

For the practice of such preferred aspects of the present invention, amino acids of the transmembrane domain are numbered by relative positions based on the central amino acid of a unmodified or unmutated domain, which is numbered as position 0 (for example, G460 in Dengue 2 virus), wherein amino acids proceeding toward the N terminus from the central amino acid are numbered −1, −2, etc., and amino acids proceeding toward the C-terminus from the central amino acid are numbered +1, +2, etc. For the purposes of such preferred aspects, the mutation may comprise a deletion of at least two, three, four, five or more amino acids comprising the central amino acids. Representative examples of such a mutation may comprise or consist of a deletion of amino acids at positions of 0 to +3, 0 to +4, −2 to 0, −3 to 0, or −1 to +1.

Non-limiting examples of flavivirus include Dengue viruses (DV), West Nile virus (WNV), yellow fever virus (YFV), Japanese encephalitis virus (JEV), tick-borne encephalitis virus (TBE virus), Murray Valley encephalitis virus (MVEV), Saint Louis encephalitis virus (SLEV), and Powassan virus (PV). The engineered nucleic acid sequences comprising a modified transmembrane protein, especially a modified transmembrane domain, from each of these viruses is included as part of the present invention.

The Dengue virus group may include dengue virus types 1, 2, 3, and 4. In specific particularly preferred embodiments, the mutation of Dengue virus type 2 may comprise a deletion at amino acids 458 to 460 (deletion of L458, 1459, and G460, i.e., deletion of positions-2 through 0) or at amino acids 460 to 463 (deletion of G460, V461, I462, and I463, i.e., deletion of positions 0 through +3). The virus may also be Dengue virus type 1 and the mutation may comprise a deletion at amino acids 458 to 460, amino acids 460 to 463, amino acids 457 to 460, amino acids 460 to 464, or amino acids 459 to 461. The virus may also be Dengue virus type 3 and the mutation may comprise a deletion at amino acids 456 to 458, amino acids 458 to 461, amino acids 455 to 458, amino acids 458 to 462, or amino acids 457 to 459. The virus may also be Dengue virus type 4 and the mutation may comprise a deletion at amino acids 458 to 460, amino acids 460 to 463, amino acids 457 to 460, amino acids 460 to 464, or amino acids 459 to 461. The virus may also be West Nile virus and the mutation may comprise a deletion at amino acids 463 to 465, amino acids 465 to 468, amino acids 462 to 465, amino acids 465 to 469, or amino acids 464 to 466. See examples in Table 2.

TABLE 2

Dengue and West Nile virus E-T1 Transmembrane Domain Mutants

| CloneE-T1 Domain Sequence | | Mutants | | | | |
|---|---|---|---|---|---|---|
| DEN2 $_{452}$SWTMKILIGVIITWIG$_{467}$ (SEQ ID NO: 1) | ΔGVII | ΔGVIIT | ΔLIG | ΔILIG | ΔIGV | |
| DEN1 $_{452}$SWTMKIGIGILLTWLG$_{467}$ (SEQ ID NO: 15) | ΔGILL | ΔGILLT | ΔGIG | ΔIGIG | ΔIGI | |
| DEN3 $_{450}$SWIMKIGIGVLLTWIG$_{465}$ (SEQ ID NO: 16) | ΔGVLL | ΔGVLLT | ΔGIG | ΔIGIG | ΔIGV | |

TABLE 2-continued

Dengue and West Nile virus E-T1 Transmembrane Domain Mutants

| Clone | E-T1 Domain Sequence | Mutants | | | | |
|---|---|---|---|---|---|---|
| DEN4 | $_{452}$SWMIRILIGFLVLWIG$_{467}$ (SEQ ID NO: 17) | ΔGFLV | ΔGFLVL | ΔLIG | ΔILIG | ΔIGF |
| WNV | $_{457}$SWITQGLLGALLLWMG$_{472}$ (SEQ ID NO: 18) | ΔGALL | ΔGALLL | ΔLLG | ΔGLLG | ΔLGA |

The virus comprising the modified transmembrane protein such as flavivirus E protein may have an ability to produce at least or about 100, 200, 300, 400, 500, 600, 700, 800, 900, 1000, 5000, $10^4$ fold (or any range derivable therein) more progeny virus when infecting insect cells than when infecting mammalian cells. In certain aspects, the mammalian cells are human cells. In additional aspects, the insect cells may be mosquito cells.

In a further aspect, there may be provided a modified flavivirus envelope protein encoded by an engineered nucleic acid in accordance with aspects of the present invention. In a still further aspect, there may be provided a genetically engineered flavivirus comprising an engineered nucleic acid in accordance with aspects of the present invention. In certain aspects, an immunogenic composition comprising an engineered nucleic acid or a genetically engineered flavivirus in accordance with aspects of the present invention may be also provided. In certain aspects of the immunogenic composition, the engineered nucleic acid may be comprised in a virus particle. Such an immunogenic composition may be further defined as a vaccine composition in some aspects. Furthermore, the immunogenic composition may comprise an adjuvant, a preservative, or two or more viruses or nucleic acids, which are engineered in accordance with aspects of the invention or native. For example, the vaccine composition may comprise one or more of the genetically engineered Dengue virus 1, 2, 3, and 4. In a particular aspect, the vaccine composition may comprise the genetically engineered Dengue virus type 2. For long lasting protection against all Dengue virus serotypes, the vaccine composition may comprise the genetically engineered Dengue virus of all sero types, particularly, a tetravalent vaccine composition.

Aspects of the invention may further include a method of producing a viral vaccine from the genetically engineered flavivirus for vaccination of mammals, comprising introducing the genetically engineered virus to insect cells to produce a viral vaccine. There may also be provided a method of inducing an immune response in a mammal, comprising administering the immunogenic composition to the mammal.

In a further embodiment there is provided a vaccine composition comprising one or more mutant flaviviruses, according to aspects of the invention, and pharmaceutically acceptable excipient. Thus, it will be understood that the vaccine composition may comprise any of the mutant flaviviruses described herein. In further specific embodiments, a vaccine composition may comprise sequences from two or more viruses according to the current invention. For example, the vaccine composition may comprise engineered sequences from four Dengue virus serotypes. In some embodiments, the mutant flavivirus is defective in assembly or infectivity in mammalian cells but competent to assemble in or infect insect cells due to mutations in the transmembrane domain. In other embodiments the viruses may be further inactivated. For example in some specific cases the viruses according to the invention may be inactivated by irradiation, or chemical treatment, such as formalin treatment. In further embodiments, vaccine compositions according to aspects of the invention may further comprise additional elements such as an adjuvant, an immunomodulator and/or a preservative.

In some further aspects of the invention, there is provided a method of vaccinating an animal comprising administering the vaccine composition to a mammal. The mammal may be a human or a primate, such as a monkey. For example, in some specific embodiments the vaccine composition is administered to a human, however the method may also be used to vaccinate livestock, wild and domesticated birds, cats, and dogs. In certain cases, the vaccine composition may be administered, orally, intravenously, intramuscularly, intraperitoneally, intradermally or subcutaneously. In some cases the vaccine composition is administered multiple times, and in certain cases each administration is separated by a period of days, weeks, months or years.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan; however, these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

In FIG. 3A are C6/36 and in FIG. 3B, Vero cells infected with the wild type DV virus. Virus particles are seen in large paracrystalline structures within the mosquito cell (FIG. 3A—arrows) and associated with the Vero plasma cell membrane (FIG. 3B—arrows). In FIG. 3C, are shown mosquito cells infected with the ΔGVII mutant which displayed similar amounts of virus particles to that seen in the wt virus infected mosquito cells (arrows). However, in mammalian cells infected with the same mutant (FIG. 3D ΔGVII) only the presence of nucleocapsids in the cytoplasm could be detected in the thin sections (arrowheads). In cells infected with the mutant ΔLIG similar results were observed to that of the ΔGVII mutant. The presence of virus particles could be observed in the cytoplasm of mosquito cells (FIG. 3E—arrowheads) while only nucleocapsids were detected in the cytoplasm of the Vero cells (FIG. 3F—arrowheads). Bars are 500 nM.

FIG. 10. Total IgM post challenge. Total IgM was measured by Dengue IgM ELISA kit. Each bar represents the average Antibody Index of 4 monkey serum samples per experimental group. The measurements were done on the days represented on X-axis.

DESCRIPTION OF ILLUSTRATIVE EMBODIMENTS

I. Introduction

Figure 1:
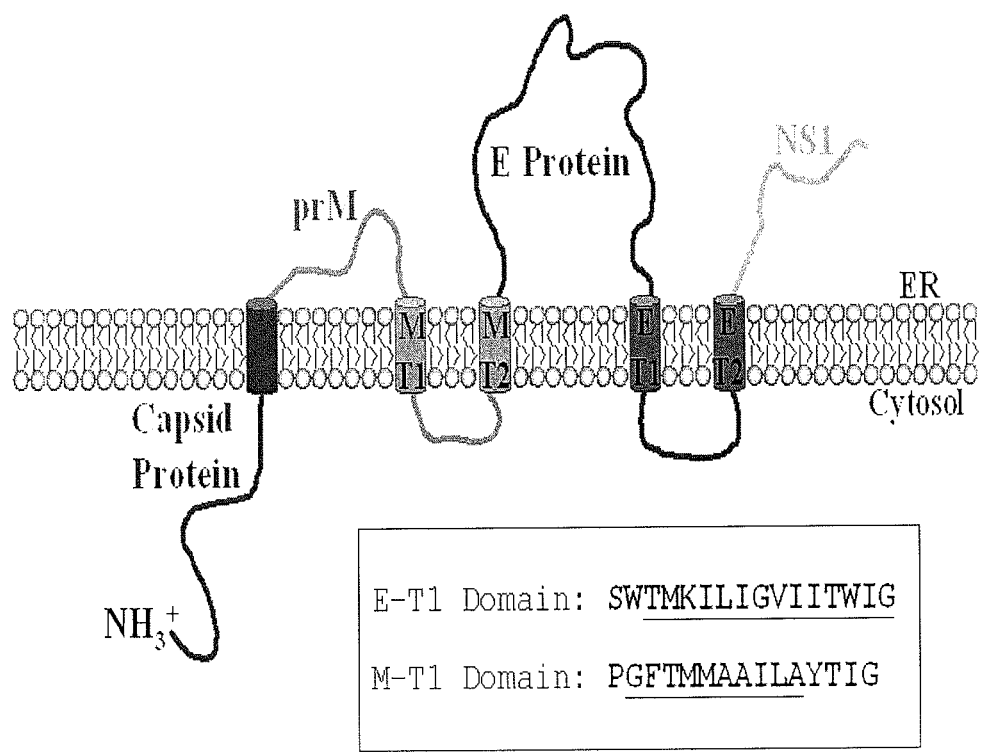
FIG. 1. Schematic representation of the organization of Dengue virus. Representation of DV protein structure illustrating the predicted orientation across the endoplasmic reticulum (ER). Cylinders represent transmembrane (T) helices. prM, membrane protein precursor; E, envelope protein; NS1, non-structural protein. The minimal predicted sequences of the E protein T1 and M protein T1 are shown. Underlined residues indicate the amino acids targeted for deletion. The TM domain of the capsid protein (anchored C) is cleaved during processing and is not present in the membrane of the assembled virus.

There are over 700 known arboviruses and at least 80 immunologically distinct types that cause disease in humans. Arboviruses are transmitted among vertebrates by biting insects, chiefly mosquitoes and ticks. These viruses are widely distributed throughout the world, depending on the presence of appropriate hosts (birds, horses, domestic animals, humans) and vectors. Mosquito-borne arboviruses present some of the most important examples of emerging and resurgent diseases of global significance. A strategy has been developed herein by which host range mutants of flavivirus such as Dengue virus can be constructed by generating deletions in the transmembrane domain of envelope (E) glycoprotein. The host range mutants produced are restricted to growth in the insect hosts and elicited antibody production in preliminary mouse trials. This method of producing vaccine strains of arboviruses like flaviviruses is novel, simple and inexpensive compared to other non-infectious vaccine platforms.

As used herein, the term "membrane-bound virus" refers to a virus which contains a lipid membrane bilayer as part of its protective exterior coat.

As used herein the term "viral envelope" refers to the lipid membrane component of the membrane containing virus and its associated proteins.

As used herein, the terms "arthropod vectored virus" or "Arbovirus" refer to viral agents which replicate and produce progeny virus in arthropod (insect) or mammalian cells. This includes Togaviruses, Flaviviruses and Bunyaviruses. As used herein, the term "Togavirus" refers to a general classification of membrane containing viruses which include the Alphaviruses.

As used herein, the term "membrane bilayer" refers to a structure consisting of opposed amphipathic phospholipids. The bilayer is organized in cross section from polar head groups to non-polar carbon chains to nonpolar carbon chains to polar head groups.

As used herein, the term "transmembrane domain" refers to the amino acid sequence of the region of a membrane-integrated protein which spans the membrane bilayer.

As used herein, the term "viral vaccine" refers to a strain of virus or virus mutant or a combination of such viruses or virus mutants which has the antigenic properties of the virus but cannot produce disease or a combination of such viruses or virus mutants.

As used herein the term "immune surveillance" refers to a process by which blood lymphocytes survey the cells and tissues of a mammal to determine the presence of foreign (virus) proteins and stimulates the production of lymphocytes capable of targeting cells producing the foreign protein for destruction. This process also leads to the production of circulating antibodies against the foreign protein.

As used herein, the term "infectious virus particles" refers to viruses which are capable of entering a cell and producing virus protein, whether or not they are capable of producing progeny virus.

As used herein, the term "non-infectious virus particles" refers to viruses which are not capable of infecting or entering a cell.

As used herein, the term "vertebrate cells" refers to any mammalian cell, such as human or monkey cells.

As used herein, the term "invertebrate cells" refers to any insect cell, such as mosquito cells.

Antigen may refer to foreign protein recognized by the immune system

"Attenuated" may refer to impaired in the ability to produce infectious virus particles.

CBC, or complete blood count, may be measured in a blood test to determine the health of an individual.

Challenge virus may refer to a highly infectious strain of virus which is administered to the host animals after the initial vaccination. It is given after a period during which the immune system should have responded to the virus. A good vaccine will not allow the challenge virus to produce significant viremia.

Efficacy may refer to the ability of a drug to produce the desired therapeutic effect or the ability of a vaccine to protect against an infection.

ELISA, or enzyme linked immunosorbent assay, refers to a colorimetric assay used to detect antibodies (Ab) against specific antigens (proteins).

Erythema refers to redness of the skin due to inflammation.

FFU, focus forming units, may be the concentration of foci of infection of any given virus/ml. It may be used in a test to measure the number of infectious virus particles in a sample. A focus is a localized infection of cells in a cell culture. It may be viewed by staining with specific Abs for a substrate that may give a colored or fluorescent product. The number of infectious virus may be referred to as the virus titer.

FRNT, or focus reduction neutralization test, refers to an assay for Ab which neutralizes virus specifically and as a result cause reduction in the number of foci. PRNT, or Plaque reduction neutralization test, differs from a focus-based test by the way the infections are visualized. Plaques can be seen with the naked eye.

Hematocrit refers to proportion of red blood cells in the blood.

IC refers to infectious centers. Foci of infection that are grown as spherical foci involving a larger volume of infected cells than a typical flat focus.

Nab, or neutralizing Ab, may refer to antibodies (Ab) produced by the immune system which will inactivate virus specifically. IgG is the most desired Ab to induce when an infection is in the blood stream. It is used as one measure of the immunogenicity of a vaccine. IgM and IgG are different types of Ab produced at different times during the immune response to antigen.

Phenotype may refer to any measurable physical or biochemical characteristics of an organism, as determined by both genetics and environment.

Real time PCR, or qPCR, refers to a biochemical measurement of the virus genetic material or RNA. It is a measure of how much virus has replicated.

Viremia may refer to the presence of virus in the bloodstream.

Wild-type virus may refer to original, parental genetic viral sequence containing no mutations.

II. Flaviviruses

In certain aspects of the invention, there may be provided compositions and methods related to modification of flavivirus proteins for generating mutations that affect host range phenotype. Therefore, flavivirus vaccine may be provided.

Flaviviruses are small, enveloped, positive-strand RNA viruses, several of which pose current or potential threats to global public health. Yellow fever virus, for example, has been the cause of epidemics in certain jungle locations of sub-Saharan Africa, as well as in some parts of South America. Although many yellow fever infections are mild, the disease can also cause severe, life-threatening illness. The disease state has two phases. The initial or acute phase is normally characterized by high fever, chills, headache, backache, muscle aches, loss of appetite, nausea, and vomiting. After three to four days, these symptoms disappear. In some patients, symptoms then reappear, as the disease enters its so-called toxic phase. During this phase, high fever reappears and can lead to shock, bleeding (e.g., bleeding from the mouth, nose, eyes, and/or stomach), kidney failure, and liver failure. Indeed, liver failure causes jaundice, which is yellowing of the skin and the whites of the eyes, and thus gives "yellow fever" its name. About half of the patients who enter the toxic phase die within 10 to 14 days. However, persons that recover from yellow fever have lifelong immunity against reinfection. The number of people infected with yellow fever virus over the last two decades has been increasing, with there now about 200,000 yellow fever cases reported, with about 30,000 deaths, each year. The re-emergence of yellow fever virus thus presents a serious public health concern.

Fully processed, mature virions of flaviviruses contain three structural proteins: capsid (C), membrane (M), and envelope (E). The infection also produces seven non-structural proteins. Immature flavivirions found in infected cells contain pre-membrane (prM) protein, which is a precursor to the M protein. The flavivirus proteins are produced by translation of a single, long open reading frame to generate a polyprotein, followed by a complex series of post-translational proteolytic cleavages of the polyprotein, to generate mature viral proteins (Amberg, 1999; Rice, 1995). The virus structural proteins are arranged in the polyprotein in the order C-prM-E.

Dengue Virus (DV), the most prevalent arbovirus, is in the family Flaviviridae and has four distinct serotypes which cause an acute disease of sudden onset with headache, fever, prostration, severe joint and muscle pain, lymphadenopathy, and rash (Martina et al., 2009; WHO, 2009). DV is transmitted by mosquitoes and as distribution and density of these has expanded, a considerable increase in Dengue virus transmission in tropical and subtropical areas throughout the world has been observed, with about 50 million cases of Dengue Fever and 500,000 cases of the more severe Dengue Hemorrhagic Fever (DHF). Over 20,000 deaths each year can be attributed to DHF, ranking Dengue with tuberculosis, STDs (including HIV), childhood diseases or malaria in costs of care and economic impact. DV is also the only known arbovirus that has fully adapted to the human host and has lost the need of an enzootic cycle for maintenance The lack of prophylactics, vaccines or antivirals against DV alone leaves 2 billion people at risk yearly to contract this disease (WHO, 2009).

DV is an enveloped virus of 40 to 50 nm diameter with an icosahedral capsid that contains a single-stranded, positive sense RNA genome (Zhang et al., 2003). The envelope of DV is composed of hetero-dimers of the (E) glycoprotein and the membrane (M) protein that are embedded in a host-derived lipid bilayer (FIG. 1). The envelope surrounds the capsid composed entirely of the capsid (C) protein which encapsulates the RNA genome. The E glycoprotein is important for cell receptor attachment, and infection of the target cell membrane, and bears the neutralization epitopes (Mukhopadhyay et al., 2005). DV has, as have all arboviruses evolved to replicate in the unique biochemical environments of both vertebrate and invertebrate hosts (Condreay and Brown, 1986). The mature viruses are hybrids which derive their lipid bilayers from the host cell. Insect cell membranes do not contain cholesterol and are thinner in cross-section (Bretscher and Munro, 1993); therefore, the membrane-spanning domains (transmembrane domains; TMD) of proteins integrated into insect cell membranes have evolved to accommodate both host membranes. The TMD of the virus grown in the insect hosts has been shown in the alphavirus Sindbis to tolerate large deletions and thus was shown not to require the same spanning length as those integrated into mammalian membranes (Hernandez et al., 2003). This host-derived TMD difference was used to develop a method for production of viral mutants with truncated TMD that are capable of efficient growth in invertebrate cells but incapable of efficient productive replication in vertebrate cells (Hernandez et al., 2003).

As demonstrated by studies herein, a targeted and rational method of deleting amino acids in the TMD of the envelope glycoproteins was used to create DV serotype 2 (DV2) mutants. Deleting amino acids in the TMD of the E or M proteins of the virus will make them shorter such that they are capable of spanning an insect but not the mammalian cell membrane and as a result will show reduced infectivity in mammalian hosts but will retain efficient growth in insect hosts, producing a host-range phenotype. This method of generating a host range phenotype has been demonstrated for Sindbis, a structurally similar but distantly related arbovirus (Hernandez et al., 2003). Deletions in the TMD of Sindbis virus (SV), the prototypical arbovirus, resulted in virus with altered infectivity and host range (Hernandez et al., 2003). Both E and M proteins of DV have a TMD that can be targeted for deletion mutation analysis using the SV TMD deletion strategy. In the Example, mutant DV2 viruses were identified as having a host range phenotype restricted to growth in insect cells. Studies herein demonstrate that truncations of 3 to 4 amino acids in the TMD of the E domain at amino acid positions (DV2 16681 numbering) between 458 to 463 resulted in virus with attenuated virulence in mammalian cells that retained the ability to grow in mosquito cells while larger deletions resulted in either no or very low levels of virus production and infectivity.

Additional flaviviruses that can be used in the invention include other mosquito-borne flaviviruses, such as Japanese encephalitis, Murray Valley encephalitis, St. Louis encephalitis, West Nile, Kunjin, Rocio encephalitis, and Ilheus viruses; tick-borne flaviviruses, such as Central European encephalitis, Siberian encephalitis, Russian Spring-Summer encephalitis, Kyasanur Forest Disease, Omsk Hemorrhagic fever, Louping ill, Powassan, Negishi, Absettarov, Hansalova, Apoi, and Hypr viruses.

In addition to the viruses listed above, as well as other flaviviruses, chimeric flaviviruses that include one or more mutations that decrease replication in mammalian cells are also included as a type of flavivirus in the invention. These chimeras can consist of a flavivirus (i.e., a backbone flavivirus) in which a structural protein (or proteins) has been replaced with a corresponding structural protein (or proteins) of a second virus (i.e., a test or a predetermined virus, such as a flavivirus). For example, the chimeras can consist of a backbone flavivirus (e.g., a yellow fever virus) in which the prM and E proteins of the flavivirus have been replaced with the prM and E proteins of the second, test virus (e.g., a dengue virus (serotypes 1-4), Japanese encephalitis virus, West Nile virus, or another virus, such as any of those mentioned herein). The chimeric viruses can be made from any combination of viruses. Preferably, the virus against which immunity is sought is the source of the inserted structural protein(s).

III. Transmembrane Domain Mutations

The vaccines of certain aspects of the present invention are based on deletion mutations in the transmembrane domains of membrane glycoproteins of membrane-enveloped viruses, especially E-T1 domain of flaviviruses. Many membrane-coated viruses have membrane glycoproteins on their surface which are responsible for identifying and infecting target cells (Schlesinger and Schlesinger, 1990). These membrane glycoproteins have hydrophobic membrane-spanning domains which anchor the proteins in the membrane bilayer (Rice et al.; 1982).

The membrane-spanning domains of these transmembrane proteins need to be long enough to reach from one side of the bilayer to the other in order to hold or anchor the proteins in the membrane. Experiments have shown that if the domains are shortened by the deletion of amino acids within the domain, the proteins do not appropriately associate with the membrane and fall out (Adams and Rose. 1985). Unlike mammalian cell membranes, the membranes of insect cells contain no cholesterol (Clayton 1964, Mitsuhashi et al., 1983). Because insects have no cholesterol in their membranes, the insect-generated viral membrane will be thinner in cross section than the viral membranes generated from mammals. Consequently, the membrane-spanning domains of proteins integrated into insect membranes do not need to be as long as those integrated into the membranes of mammals. It is possible, therefore, to produce deletions in engineered viruses which remove amino acids from the transmembrane domain of the viral glycoprotein. This results in a glycoprotein which can integrate normally into the membrane of a virus replicating in an insect cell, but not into the membrane of a virus replicating, infecting, or assembling normally in a mammalian cell. Thus, the mutated virus can replicate and be produced in insect cells as well as the parent wild-type virus. On the other hand, the mutant virus can infect mammalian cells and produce viral proteins; however, since the mutated virus glycoprotein cannot span and be anchored in the mammalian membrane, progeny virus cannot be produced in mammalian cells to wild-type levels. An advantage to the approach of the present invention is that the mutants are engineered as deletion mutants, and preferably deletion of at least two or three amino acids, hence there is little chance for reversion to wild-type phenotype, a common problem with virus vaccines.

The methods and compositions described by the present invention may work for any virus which replicates in insects and mammals and has integral membrane proteins as part of its structure, namely, Togaviruses, Flaviviruses and Bunya viruses and all other enveloped viruses which can replicate naturally in both mammalian and insect cells, as well as enveloped viruses which can be made to replicate in mammalian and insect cells by genetic engineering of either the virus or the cell.

Vaccines may be made against any membrane-containing virus by removing amino acids from the membrane-spanning domain of a protein in the viral envelope. This is preferably done by removing nucleotides from a cDNA clone of the virus as described below. RNA transcribed from the altered clone may be then transfected into insect cells. The viruses produced are amplified by repeated growth in insect cells until large quantities of mutant viruses are obtained. These viruses are tested for the ability to infect and produce progeny in mammalian cells. Viruses which produce little to no progeny in mammalian cells are tested for ability to produce immunity in laboratory animals. Those viruses which do produce immunity are candidates for production of human and animal vaccines by procedures known in the art. Non-limiting examples of Flavivirus mutants are shown below in Table 2. Glycine (G) in the center of E-T1 transmembrane domain (amino acid (aa) G460 in Dengue serotypes 1, 2, and 4; aa G458 in Dengue 3; and aa G465 in West Nile virus) is designated as position zero in accordance with aspects of the present invention.

In certain embodiments mutant viruses according to the current invention may comprise two or more host range mutations or additionally comprise other mutations such as attenuating mutations, mutations to increase immunogenicity or viral stability or any mutations that may be used for vaccine production and that are current known in the art.

IV. Viral Vaccine

Certain aspects of the present invention are drawn to a method of producing a viral vaccine from the genetically engineered membrane-enveloped virus disclosed herein for vaccination of mammals, comprising the steps of introducing the engineered virus into insect cells and allowing the virus to replicate in the insect cells to produce a viral vaccine. Representative examples of the engineered viruses are Dengue virus E-T1 mutants (for example deletion of GVII or LIG).

Both DV host range mutations identified produced a significant numbers of non-infectious virions. This was a phenotype also associated with mutants of Sindbis virus, a member of alphavirus family. A significant difference in the assembly of alpha and flaviviruses is the association of the glycoprotein-modified viral membrane with the nucleocapsid. Alphaviruses are characterized by the strong association of the E2 tail with the nucleocapsid which is required for assembly and infectivity (West et al., 2006). The flaviviruses do not directly interact with the nucleocapsid and the mechanism by which virus budding occurs in association with the core is not known (Murray et al., 2008; Samsa et al., 2009). Additionally, flaviviruses produce empty particles (Lobigs and Lee, 2004; Lobigs et al., 2004; Murray et al., 2008) which increase toward late stages of infection suggesting that some component (viral or host) is depleted as the infection progresses. These specific differences in the details of virus assembly in the alpha and flavivirus systems underscore the importance of the membrane in the host range phenotype. It is for this reason that it is expected that this technology can be applied to other flaviviruses and arboviruses.

It is contemplated in certain aspects of the invention that one, two, three, four or more of these types of mutations can be combined, for example, to use constructs of DV1-4 in order to formulate a tetravalent vaccine. This is a novel approach which only requires molecular biology methods until the mutants are identified. This combination of host range mutants for DV1-4 would constitute a live virus vaccine grown in insect cells. The DV host range mutants were shown not to revert to wild type after multiple passages displaying genetic stability in the host used for production. The reasons for this characteristic are not known but alphavirus complementation does not occur in insect cells implying component sequestration (Condreay and Brown. 1986; Renz and Brown. 1976). These data provide further evidence that sequence elements which define host range are expressed throughout the arbovirus genome. This host range mutant methodology could continue to be applied to other pathogenic flaviviruses and alphaviruses to produce vaccine strains.

Furthermore, certain aspects of the present invention provide a method of producing a viral vaccine to a disease spread by a wild mosquito population to a mammal, comprising the steps of genetically engineering a deletion of one or more amino acids in a flavivirus E protein such as the E-T1 domain to produce an engineered virus, wherein the transmembrane protein is able to span the membrane envelope when the virus replicates in mosquito cells, but is unable to efficiently span the membrane envelope when the virus replicates in mammalian cells, and wherein the virus remains capable of replicating in mosquito cells; introducing the engineered virus into a wild mosquito population; and allowing the virus to replicate in cells of the wild mosquito population to produce a population of mosquitoes which excludes the wild type pathogenic virus and harbors the vaccine strain of the virus such that the mosquito bite delivers the vaccine to a mammal bitten.

In addition, certain aspects of the present invention provide a method of vaccinating an individual in need of such treatment, comprising the steps of introducing the viral vaccine of the present invention into the individual and allowing the vaccine to produce viral proteins for immune surveillance and stimulate the immune system for antibody production in the individual.

A. Vaccine Preparations

In any case, a vaccine component (e.g., an antigenic peptide, polypeptide, nucleic acid encoding a proteinaceous composition or virus particle) may be isolated and/or purified from the chemical synthesis reagents, cell or cellular components. In a method of producing the vaccine component, purification is accomplished by any appropriate technique that is described herein or well known to those of skill in the art (e.g., Sambrook et al., 1987). Although preferred for use in certain embodiments, there is no general requirement that an antigenic composition of the present invention or other vaccine component always be provided in their most purified state. Indeed, it is contemplated that less substantially purified vaccine component, which is nonetheless enriched in the desired compound, relative to the natural state, will have utility in certain embodiments, such as, for example, total recovery of protein product, or in maintaining the activity of an expressed protein. However, it is contemplated that inactive products also have utility in certain embodiments, such as, e.g., in determining antigenicity via antibody generation.

Certain aspects of the present invention also provide purified, and in preferred embodiments, substantially purified vaccines or vaccine components. The term "purified vaccine component" as used herein, is intended to refer to at least one vaccine component (e.g., a proteinaceous composition, isolatable from cells), wherein the component is purified to any degree relative to its naturally obtainable state, e.g., relative to its purity within a cellular extract or reagents of chemical synthesis. In certain aspects wherein the vaccine component is a proteinaceous composition, a purified vaccine component also refers to a wild type or mutant protein, polypeptide, or peptide free from the environment in which it naturally occurs.

Where the term "substantially purified" is used, this will refer to a composition in which the specific compound (e.g., a protein, polypeptide, or peptide) forms the major component of the composition, such as constituting about 50% of the compounds in the composition or more. In preferred embodiments, a substantially purified vaccine component will constitute more than about 60%, about 70%, about 80%, about 90%, about 95%, about 99% or even more of the compounds in the composition.

In certain embodiments, a vaccine component may be purified to homogeneity. As applied to the present invention, "purified to homogeneity," means that the vaccine component has a level of purity where the compound is substantially free from other chemicals, biomolecules or cells. For example, a purified peptide, polypeptide or protein will often be sufficiently free of other protein components so that degradative sequencing may be performed successfully. Various methods for quantifying the degree of purification of a vaccine component will be known to those of skill in the art in light of the present disclosure. These include, for example, determining the specific protein activity of a fraction (e.g., antigenicity), or assessing the number of polypeptides within a fraction by gel electrophoresis.

It is contemplated that an antigenic composition of the invention may be combined with one or more additional components to form a more effective vaccine. Non-limiting examples of additional components include, for example, one or more additional antigens, immunomodulators or adjuvants to stimulate an immune response to an antigenic composition of the present invention and/or the additional component(s). For example, it is contemplated that immunomodulators can be included in the vaccine to augment a cell or a patient's (e.g., an animal's) response. Immunomodulators can be included as purified proteins, nucleic acids encoding immunomodulators, and/or cells that express immunomodulators in the vaccine composition.

Immunization protocols have used adjuvants to stimulate responses for many years, and as such adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation.

Optionally, adjuvants that are known to those skilled in the art can be used in the administration of the viruses of the invention. Adjuvants that can be used to enhance the immunogenicity of the viruses include, for example, liposomal formulations, synthetic adjuvants, such as (e.g., QS21), muramyl dipeptide, monophosphoryl lipid A, or polyphosphazine. Although these adjuvants are typically used to enhance immune responses to inactivated vaccines, they can also be used with live vaccines. In the case of a virus delivered via a mucosal route, for example, orally, mucosal adjuvants such as the heat-labile toxin of *E. coli* (LT) or mutant derivations of LT can be used as adjuvants. In addition, genes encoding cytokines that have adjuvant activities can be inserted into the viruses. Thus, genes encoding cytokines, such as GM-CSF, IL-2, IL-12, IL-13, or IL-5, can be inserted together with foreign antigen genes to produce a vaccine that results in enhanced immune responses, or to modulate immunity directed more specifically towards cellular, humoral, or mucosal responses.

An immunologic composition of the present invention may be mixed with one or more additional components (e.g., excipients, salts, etc.) which are pharmaceutically acceptable and compatible with at least one active ingredient (e.g., antigen). Suitable excipients are, for example, water, saline, dextrose, glycerol, ethanol and combinations thereof.

An immunologic composition of the present invention may be formulated into the vaccine as a neutral or salt form. A pharmaceutically acceptable salt, includes the acid addition salts (formed with the free amino groups of the peptide) and those which are formed with inorganic acids such as, for example, hydrochloric or phosphoric acid, or such organic acids as acetic, oxalic, tartaric, mandelic, and the like. A salt formed with a free carboxyl group also may be derived from an inorganic base such as, for example, sodium, potassium, ammonium, calcium, or ferric hydroxide, and such organic bases as isopropylamine, trimethylamine, ethylamino ethanol, histidine, procaine, and combinations thereof.

In addition, if desired, an immunologic composition may comprise minor amounts of one or more auxiliary substances such as for example wetting or emulsifying agents, pI-I buffering agents, etc. which enhance the effectiveness of the antigenic composition or vaccine.

B. Vaccine Administration

The viruses of the invention can be administered as primary prophylactic agents in adults or children at risk of infection, or can be used as secondary agents for treating infected patients. For example, in the case of yellow fever/dengue chimeras, the vaccines can be used in adults or children at risk of Dengue infection, or can be used as secondary agents for treating Dengue-infected patients. Examples of patients who can be treated using the dengue-related vaccines and methods of the invention include (i) children in areas in which Dengue is endemic, such as Asia, Latin America, and the Caribbean, (ii) foreign travelers, (iii) military personnel, and (iv) patients in areas of a Dengue virus epidemic. Moreover, inhabitants of regions into which the disease has been observed to be expanding (e.g., Argentina, Chile, Australia, parts of Africa, southern Europe, the Middle East, and the southern United States), or regions in which it may be observed to expand in the future (e.g., regions infested with *Aedes aegypli*, or *Aedes albopictus*), can be treated according to the invention.

Formulation of the viruses of the invention can be carried out using methods that are standard in the art. Numerous pharmaceutically acceptable solutions for use in vaccine preparation are well known and can readily be adapted for use in the present invention by those of skill in this art. (See, e.g., Remington's Pharmaceutical Sciences, 18$^{th}$ Ed., 1990) In two specific examples, the viruses are formulated in Minimum Essential Medium Earle's Salt (MEME) containing 7.5% lactose and 2.5% human serum albumin or MEME containing 10% sorbitol. However, the viruses can simply be diluted in a physiologically acceptable solution, such as sterile saline or sterile buffered saline. In another example, the viruses can be administered and formulated, for example, in the same manner as the yellow fever 17D vaccine, e.g., as a clarified suspension of infected chicken embryo tissue, or a fluid harvested from cell cultures infected with the chimeric yellow fever virus. Preferably, virus can be prepared or administered in FDA-approved insect cells.

The vaccines of the invention can be administered using methods that are well known in the art, and appropriate amounts of the vaccines administered can be readily be determined by those of skill in the art. For example, the viruses of the invention can be formulated as sterile aqueous solutions containing between $10^2$ and $10^7$ infectious units (e.g., plaque-forming units or tissue culture infectious doses) in a dose volume of 0.1 to 1.0 ml, to be administered by, for example, intramuscular, subcutaneous, or intradermal routes. In addition, because flaviviruses may be capable of infecting the human host via the mucosal routes, such as the oral route (Gresikova et al., 1988), the viruses can be administered by mucosal routes as well. Further, the vaccines of the invention can be administered in a single dose or, optionally, administration can involve the use of a priming dose followed by a booster dose that is administered, e.g., 2-6 months later, as determined to be appropriate by those of skill in the art.

The manner of administration of a vaccine may be varied widely. Any of the conventional methods for administration of a vaccine are applicable. For example, a vaccine may be conventionally administered intravenously, intradermally, intraarterially, intraperitoneally, intralesionally, intracranially, intraarticularly, intraprostaticaly, intrapleurally, intratracheally, intranasally, intravitreally, intravaginally, intratumorally, intramuscularly, intraperitoneally, subcutaneously, intravesicularlly, mucosally, intrapericardially, orally, rectally, nasally, topically, in eye drops, locally, using aerosol, injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18$^{th}$ Ed., 1990, incorporated herein by reference).

A vaccination schedule and dosages may be varied on a patient by patient basis, taking into account, for example, factors such as the weight and age of the patient, the type of disease being treated, the severity of the disease condition, previous or concurrent therapeutic interventions, the manner of administration and the like, which can be readily determined by one of ordinary skill in the art.

A vaccine is administered in a manner compatible with the dosage formulation, and in such amount as will be therapeutically effective and immunogenic. For example, the intramuscular route may be preferred in the case of toxins with short half lives in vivo. The quantity to be administered depends on the subject to be treated, including, e.g., the capacity of the individual's immune system to synthesize antibodies, and the degree of protection desired. The dosage of the vaccine will depend on the route of administration and will vary according to the size of the host. Precise amounts of an active ingredient required to be administered depend on the judgment of the practitioner. In certain embodiments, pharmaceutical compositions may comprise, for example, at least about 0.1% of an active compound. In other embodiments, the active compound may comprise between about 2% to about 75% of the weight of the unit, or between about 25% to about 60%, for example, and any range derivable therein. However, a suitable dosage range may be, for example, of the order of several hundred micrograms active ingredient per vaccination. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per vaccination, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. A suitable regime for initial administration and booster administrations (e.g., inoculations) are also variable, but are typified by an initial administration followed by subsequent inoculation(s) or other administration(s).

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1.5 years, usually three years, will be desirable to maintain protective levels of the antibodies.

The course of the immunization may be followed by assays for antibodies for the supernatant antigens. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays. Other immune assays can be performed and assays of protection from challenge with the flavivirus can be performed, following immunization.

Certain aspects of the present invention include a method of enhancing the immune response in a subject comprising the steps of contacting one or more lymphocytes with a flavivirus immunogenic composition, wherein the antigen comprises as part of its sequence a sequence nucleic acid or amino acid sequence encoding mutant E protein, according to the invention, or a immunologically functional equivalent thereof. In certain embodiments the one or more lymphocytes is comprised in an animal, such as a human. In other embodiments, the lymphocyte(s) may be isolated from an animal or from a tissue (e.g., blood) of the animal. In certain preferred embodiments, the lymphocyte(s) are peripheral blood lymphocyte(s). In certain embodiments, the one or more lymphocytes comprise a T-lymphocyte or a B-lymphocyte. In a particularly preferred facet, the T-lymphocyte is a cytotoxic T-lymphocyte.

The enhanced immune response may be an active or a passive immune response. Alternatively, the response may be part of an adoptive immunotherapy approach in which lymphocyte(s) are obtained with from an animal (e.g., a patient), then pulsed with composition comprising an antigenic composition. In a preferred embodiment, the lymphocyte(s) may be administered to the same or different animal (e.g., same or different donors).

V. Pharmaceutical Compositions

It is contemplated that pharmaceutical compositions may be prepared using the novel mutated viruses of certain aspects of the present invention. In such a case, the pharmaceutical composition comprises the novel virus and a pharmaceutically acceptable carrier. A person having ordinary skill in this art readily would be able to determine, without undue experimentation, the appropriate dosages and routes of administration of this viral vaccination compound. When used in vivo for therapy, the vaccine of certain aspects of the present invention is administered to the patient or an animal in therapeutically effective amounts, i.e., amounts that immunize the individual being treated from the disease associated with the particular virus. It may be administered parenterally, preferably intravenously or subcutaneously, but other routes of administration could be used as appropriate. The amount of vaccine administered may be in the range of about $10^3$ to about $10^6$ pfu/kg of patient weight. The schedule will be continued to optimize effectiveness while balancing negative effects of treatment. See Remington's Pharmaceutical Science, 17th Ed., (1990); and Klaassen In: Goodman and Gilman's: The Pharmacological Basis of Therapeutics, $8^{th}$ Ed. (1990); which are incorporated herein by reference. For parenteral administration, the vaccine may be formulated in a unit dosage injectable form (solution, suspension, emulsion) in association with a pharmaceutically acceptable parenteral vehicle. Such vehicles are preferably non-toxic and non-therapeutic. Examples of such vehicles are water, saline, Ringer's solution, dextrose solution, and 5% human serum albumin.

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Host Range Mutants of DV2

Figure 2:
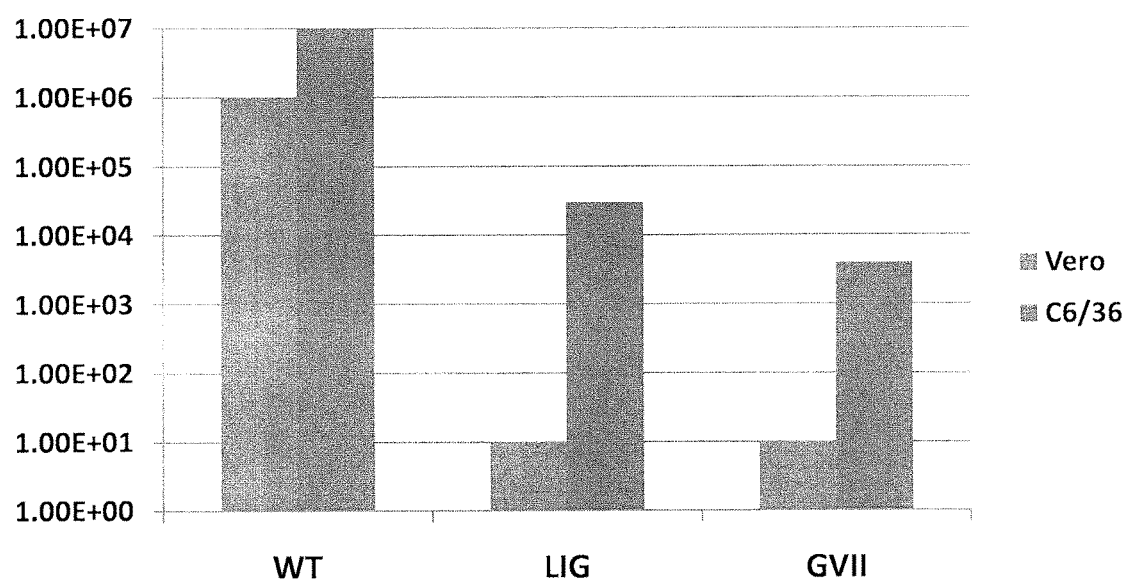
FIG. 2. Host-range phenotype of DV mutants. Titers for the DV2 WT and mutant viruses are shown. All virus strains were grown in Vero (mammalian) and the C6/36 (insect) cells to measure host-range phenotype. The titers of the mutant viruses and WT viruses were measured in the Vero cell line by the fluorescent focus assay.

Deletion mutants constructed around a specific TMD position/region exhibit host range phenotype. Two mutants DV2ΔLIG and DV2ΔGVII showed host range phenotype restricted to preferential growth in the insect cells (FIG. 2). Mutant viruses with preferential growth in the C6/36 mosquito cell line and attenuated growth in Vero cells as defined by at least 2 orders of magnitude less virus production are considered to have host range phenotype. The deletion mutants infected both Vero and C6/36 cells at a known MOI with a titer >$10^4$ FFU/ml. The Vero and C6/36 cells were infected with the mutants at MOI ~0.03 FFU/cell. The mutant viruses were grown in each cell line, harvested on day 7 and titered on Vero cells, and showed the host range phenotype. The WT DV2 routinely generates titers of $10^6$ ffu/ml in Vero cells and $10^7$ ffu/ml in C6/36 cells. Titers were in the range of $10^3$-$10^4$ ffu/ml for both DV2ΔGVII and DV2ΔLIG mutants grown in C6/36 cells (FIG. 2).

Expression and processing of DV2 host-range mutants. The two DV2 host-range mutants DV2ΔGVII and DV2ΔLIG were found to produce infectious virus, as observed in the focus assay. In order to determine if all viral proteins were indeed produced and processed as WT DV2, a western blot analysis was performed. Virus grown in mosquito cells was harvested from the cell supernatant at day 7 post-infection and examined by SDS-PAGE. To confirm the presence of specific DV proteins, the gel was transferred to substrate and blotted with an anti-DV antibody. Visualization of the protein bands revealed a similar banding pattern to that of WT DV2, verifying the correct production of virus proteins by the mutants.

Figures 3A, 3B, 3C, 3D, 3E, 3F:
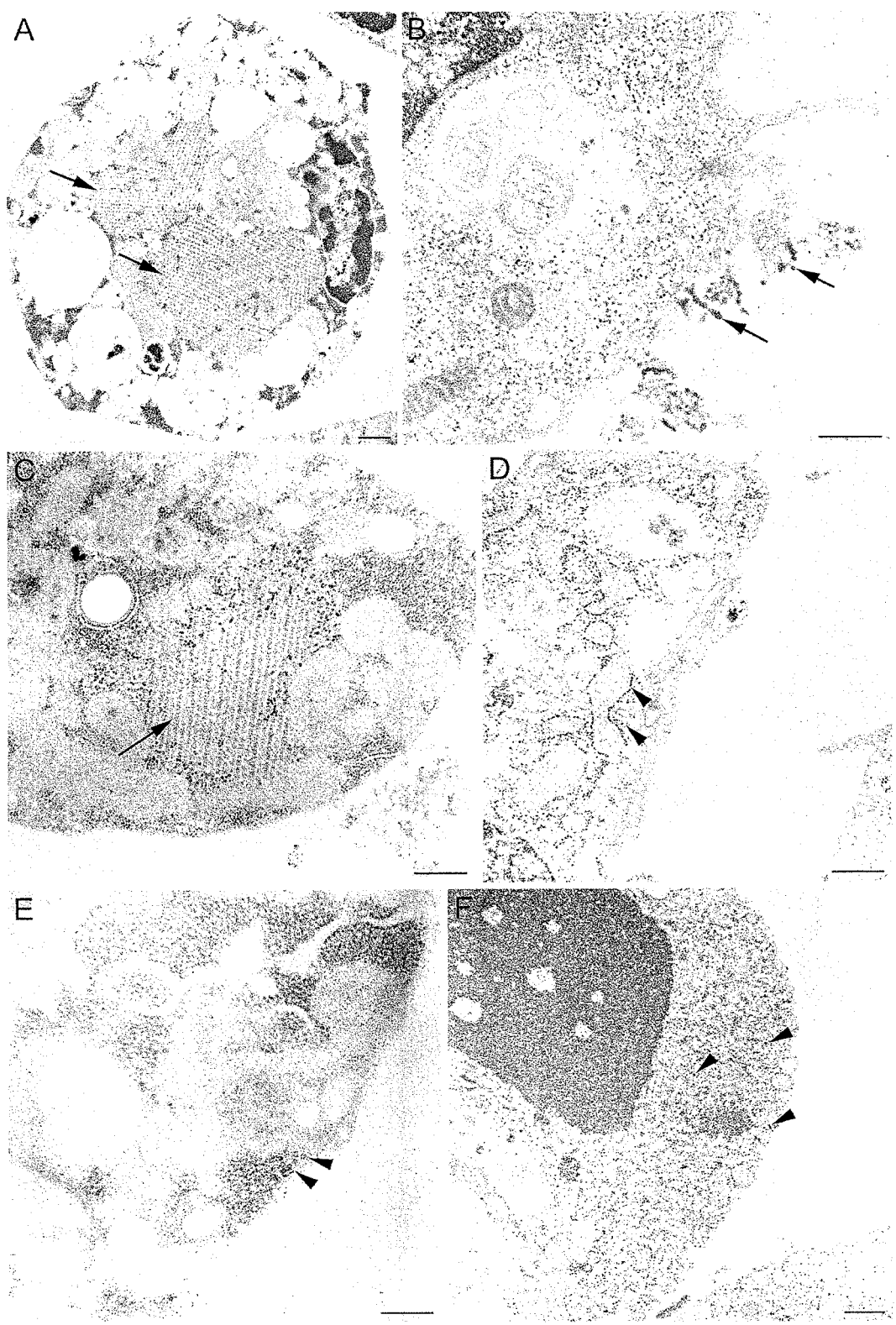
FIGS. 3A-3F. Electron microscopy of WT DV, ΔLIG, ΔGVII viruses in C6/36 and Vero cells. Shown in FIGS. 3A-3F are thin sections of the DV strains studied.

Electron micrographs of the mutants (ΔGVII and ΔLIG) suggest impaired assembly. In order to analyze the differences in virus production between mammalian and mosquito cells, thin sections of cells infected with wild type and mutant viruses were prepared and evaluated. In FIG. 3A, C6/36 and in FIG. 3B, Vero cells were infected with the wild type virus respectively. Virus particles are seen in large paracrystalline structures within the mosquito cell (FIG. 3A—arrows) and associated with the mammalian plasma cell membrane (FIG. 3B—arrows). In FIG. 3C, are shown mosquito cells infected with the ΔGVII mutant which exhibited similar amounts of virus production (arrows). However, in mammalian cells infected with the same mutant FIG. 3D only the presence of nucleocapsids in the cytoplasm could be detected in the thin sections (arrowheads) suggesting a defect in budding. In cells infected with the mutant ΔLIG similar results were observed. The presence of virus particles could be observed in the cytoplasm of mosquito cells (FIG. 3E—arrowheads) and nucleocapsids were detected in the cytoplasm of mammalian cells (FIG. 3F—arrowheads). The specific defect in the assembly pathway of these mutants in Vero cells is not known. However these results clearly demonstrate differences in virus production between these two cell types as expected for host range mutants.

Particle to FFU ratios of ΔGVII and ΔLIG from C6/36 cells. The ultrastructural analysis of the host range mutant infected cells and the large quantities of protein produced from the insect cell cultures indicated that these mutations were producing large numbers of non-infectious virus. To determine if this was indeed the case, the particle/ffu ratios were determined for each of the DV2 strains. The wild type DV strains reproducibly displays a particle to ffu ratio of $10^3$ particles/ffu. The particle to ffu ratios for the mutants DV2ΔGVII and DV2ΔLIG were assayed at $5.5 \times 10^7$ and $1.4 \times 10^7$ particles/ffu respectively. Thus, for each strain, infectious titer added to the particle to ffu ratio gives a total particle/ml quantity of ~$10^{10}$ virus particles.

Mutants with host range phenotype generate neutralizing antibody response in BALB/cJ mice. Mutants showing an insect cell preferential host range phenotype were analyzed for the ability to generate neutralizing antibodies in BALB/cJ mice. First, a mouse trial was conducted with WT DV2. BALB/cJ mice (n=5) injected subcutaneously (SC) with $10^6$ ffu/mouse and $10^5$ ffu/mouse of WT DV2, followed by a booster dose on Day 14, generated antibody titers at 50% neutralization of virus (ND$_{50}$; the serum dilution of antibody needed to inactivate 50% of virus) in the range of 8-256 ND$_{50}$ and 32-256 ND$_{50}$ respectively. These experiments demonstrated that for WT DV2 an initial dose of 10$^5$ to 10$^6$ ffu/ml followed by a booster dose on Day 14 is required to generate an immune response in mice. This experiment was repeated with the host range mutants DV2ΔGVII and DV2ΔLIG (Table 3).

As shown in Table 3, the mouse trial was conducted to determine if the host range mutants were able to generate an immune response in mice. Five groups (n=5) of 8 week old BALB/cJ mice were inoculated subcutaneously with 29 μg (~10$^2$-10$^3$ ffu/mouse) of the WI DV2, DV2ΔLIG, DV2ΔGVII, iodixanol buffer alone and mock control. The mice were boosted with an equal dose on Day 14 and the serum samples were collected from all groups on Day 28.

TABLE 3

Mouse trial design

| Groups | Number of mice | Booster Day 14 | Bleed Day 28 |
|---|---|---|---|
| WT DV2 | 5 | ✓ | ✓ |
| DV2ΔLIG | 5 | ✓ | ✓ |
| DV2ΔGVII | 5 | ✓ | ✓ |
| Buffer (Mock) | 5 | — | ✓ |

Figure 4:
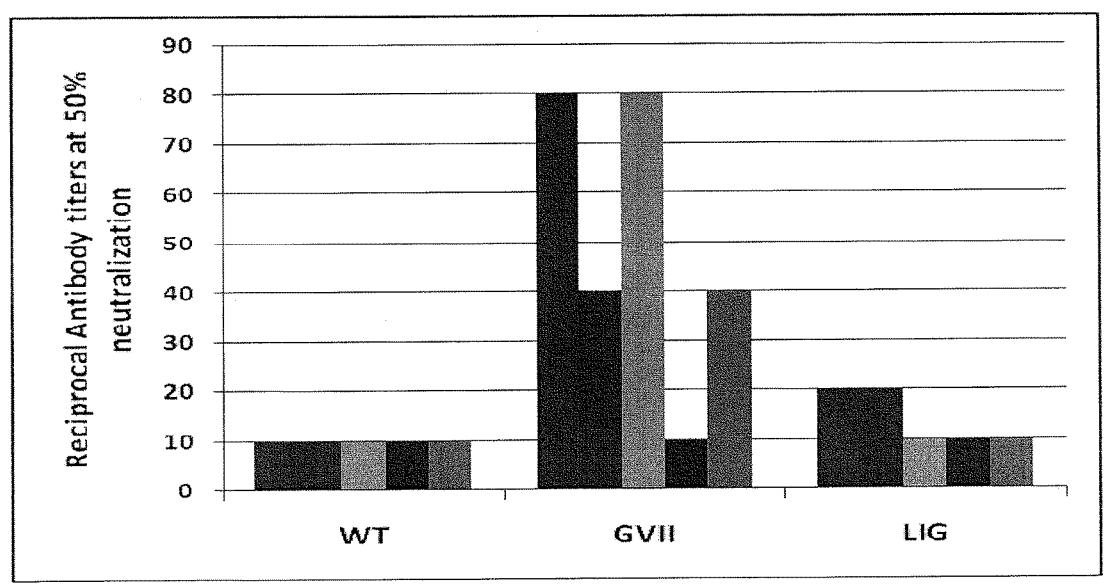
FIG. 4. Mouse Neutralizing Antibody (Nab) data. The neutralizing antibody titers were measured by the focus reduction neutralization assay using WI DV2 and sera from each individual mouse infected with the mutant virus DV2ΔLIG or DV2ΔGVII. The assay was done on Vero cells. Individual mouse serum from five mice in each group was analyzed and the titers are shown above as bars. Each bar represents the reciprocal neutralization antibody titer at 50% neutralization for each mouse.

For the mouse trials with the host range mutants the inoculum was given as protein units. For each of the groups, 29 μg of protein were injected. Both mutants were able to generate reciprocal neutralizing antibody titers in the range of 10-80 ND$_{50}$. Mice inoculated with DV2ΔGVII gave a higher neutralizing antibody response than from DV2ΔLIG and WT DV2. Four out of 5 mice in the DV2ΔGVII group gave an ND$_{50}$ between the range of 20-80 while 2 mice were responders in the DV2ΔLIG group and gave an ND$_{50}$ of ~20 (FIG. 4). Mice injected with buffer alone exhibited no neutralizing antibody response.

Mutant viruses grown in C6/36 cells are stable and do not revert to wild type virus. The host-range mutant viruses identified in this study propagate two orders of magnitude less virus than the WT virus in insect cells. These host range mutants, however, still produce two to three orders of magnitude less infectious virus from the Vero cells. As a result, there would seem to be some selective pressure on the mutant viruses to revert to the WI virus in the insect system. To confirm whether or not this was the case, reversion of the mutant viruses to WT in the C6/36 cells was evaluated over five serial passages. The cell culture supernatant was collected from the infection after each round of infection and the sequence of viral RNA was analyzed by RT-PCR as described above. It was found that the mutant viruses retained the deletions after 5 sequential passages and there was no reversion to the WT DV2 sequence. The same experiment was applied to virus grown in Vero cells. After four serial passages in the Vero cells, no WT virus RNA was recovered.

Methods

Cell Culture. C6/36 cells (*Aedes albopictus*, American Type Culture Collection [ATCC] # CRL-1660, Manassas, Va.) were maintained in minimal essential medium (MEM) containing Earl's salts supplemented with 10% fetal bovine serum (FBS), 5% tryptose phosphate broth (TPB) and 2 mM L-glutamine. Vero cells (African Green monkey kidney, ATCC #CCL-81) were maintained in 1×MEM supplemented with 10% FBS, 5% TPB, 2 mM glutamine, 10 mM Hepes pH 7.4 and 1×MEM nonessential amino acids (NEAA) (1:100 dilution of NEAA from Gibco #11140, Carlsbad, Calif.).

Construction of DV2 deletion mutants. A full-length cDNA clone of Dengue serotype 2 (DV2; Thai strain 16681, GenBank # U87411) in pGEM3z+was obtained from the Walter Reed Army Institute of Research for these studies (Irie et al., 1989). The clone produces full-length DV2 RNAs when transcribed in vitro with T7 RNA polymerase and after transfection of the transcripts into mammalian or insect cells, infectious virions are generated.

Deletions in the TMD of the DV2 E and M proteins were produced by polymerase chain reaction (PCR)-based site-directed mutagenesis, using Pfu Turbo® DNA polymerase AD (Stratagene, La Jolla, Calif.). Primers were designed to create sets of single, double, triple, quadruple, and quintuple amino acid (aa) deletions within the T1 domain of the E or M protein of DEN2. PCR conditions were as follows: 25 ng DV2 DNA, 1× or 1.5× Flit Turbo Buffer, 0.4 mM/μL dNTPs (New England Biolabs, Ipswich, Mass.), 5 ng/μL each primer, and 0.1 U/μL Pfu Turbo DNA polymerase AD. Reactions were run with and without DMSO (4% final concentration). PCR cycles were as follows: 95° C. for 2 min, then 25 cycles of 95° C. for 15 sec, 45 sec of annealing (T$_A$=Primer T$_m$-5° C. for each set of primers), 68° C. for 24 min. Extension was performed for 28 min at 68° C.; samples were held at 4° C. until analysis by gel electrophoresis. Following mutagenesis of the WT DV2 clone, the PCR products were digested with DpnI (New England Biolabs) and transformed into SURE®2 Supercompetent *E. coli* cells (Stratagene) as per manufacturer's instructions with a few alterations. Following heat shock and recovery on ice, room temperature NZY$^+$ broth (Teknova, Hollister, Calif.) was added and incubation was performed at 30° C. for 1 to 2 hours with shaking. After plating on Luria Broth (LB) agar containing 50 μg/mL carbenicillin (Teknova) incubation was performed at 30° C. for 32 to 48 hours. A colony PCR screen was then used to quickly identify the presence of the mutations in the resulting bacterial colonies prior to culture. Growth of all DV2 clones in SURE®2 cells was conducted in LB containing 50 μg/mL carbenicillin at 28 to 30° C. for approximately 24 to 48 hours with shaking. DV2 plasmid DNA was recovered using the Wizard® Plus Minipreps DNA Purification System (Promega, Madison, Wis.) following manufacturer's instructions. All DV2 deletion mutant clones were confirmed by sequence analysis (Eurofins MWG Operon, Huntsville, Ala.).

In vitro transcription and RNA transfection. Transcripts were generated for each DV2 mutant clone using the RiboMAX™ Large Scale RNA Product Systems for T7 RNA Polymerase (Promega) following manufacturer's instructions, with the addition of RNA cap analog 7 mg (ppp)G (NEB # S1404S). The RNA transcripts were transfected into Vero and C6/36 cells as follows: Cells were pelleted and washed in RNase free electroporation buffer (PBS-D for Vero and MOPS for C6/36) and resuspended in their respective buffers at a concentration of 1×10$^7$ to 5×10$^7$ cells/ml. RNA transcripts were added to 400 μl of cells and electroporated at 1.0 KV, 50 μF and ∞ resistance using the BioRad Gene Pulsar II (Bio-Rad Laboratories, Hercules, Calif.). The transfected cells were then plated at different concentrations in three different 24 well plates with 1.0 ml of the media and incubated at 37° C. for Vero cells and 28° C. for C6/36 cells for 1 hour with slow rocking. The media was removed and the plates overlayed with 1.0 ml of 1% carboxymethylcellulose (CMC) in 1× Vero media or 1×C6/

36 media and incubated for 7, 10 and 14 days. The plates were developed by focus assay.

Focus assay. The focus assay may be developed as a colorimetric or fluorescent assay using antibodies labeled with either HRPO (color substrate) or Alexa Fluor fluorescent dye. For the color assay, plates with transfected or infected cells were washed twice with 1×PBS and fixed with 80% methanol for 15 minutes at room temperature, followed by incubation with antibody dilution buffer (5% skim milk in 1×PBS-D) for 10 minutes. Primary antibody (α-DV NS1 glycoprotein, Abcam #ab41623, Cambridge, Mass.) was added at a dilution of 1:400 in antibody (Ab) dilution buffer and incubated for 1 hour at 37° C. with slow rocking. The wells were then washed twice with 1×PBS followed by the addition of secondary antibody conjugated with horse radish peroxidase (HRP) (Sigma # 8924, St. Louis, Mo.) at a dilution of 1:500 in Ab dilution buffer. Wells were washed again twice with 1×PBS. Foci were visualized by the addition of 150 µl TrueBlue™ peroxidase substrate (KPL# 50-78-02, Gaithersburg, Md.) to each well and developing for ~15 minutes. Foci were counted and titer determined in focus forming units/ml (ffu/ml) of virus. For the fluorescent assay, the protocol is similar to the color assay with the following exceptions: Cells are fixed for 20 minutes at room temperature in 100% methanol. A second 10 minute incubation with 1×PBS plus 0.05% Tween, followed by 2 washes with 1×PBS plus 0.2% BSA. Antibody is diluted in 1×PBS+0.2% BSA. The washes between the primary and secondary antibodies are performed in 1×PBS+0.2% BSA. The secondary antibody, Alexa fluor® 488 F(ab')$_2$ fragment of goat anti-mouse IgG (Invitrogen # A-11017, Carlsbad, Calif.), incubation is conducted for 45 minutes in darkness. After the final wash, 50 µl of water is added to each well for visualization of the fluorescent foci.

Infection and purification of selected mutants. The WT and DV2 mutants were grown in the *Aedes albopictus* mosquito-derived C6/36 cell line. Cells were split one day prior to infection at a ratio of 1:3. Subconfluent monolayers of C6/36 cells were infected at an MOI of ~0.03 ffu/cell. Virus was diluted in C6/36 media and each 75 cm$^3$ flask infected with 1.0 ml of diluted virus for 1 hour at room temperature with slow rocking. After the initial infection, 4.0 ml of fresh media was added to each flask. Flasks were then incubated for 7 days at 28° C. Virus was harvested by centrifugation of the supernatant at 4000 rpm for 10 min. Purification and concentration of WT and mutant DV2 were achieved using isopycnic ultracentrifugation with iodixanol (Optiprep) gradients (Sigma, St. Louis, Mo.). Virus was spun to equilibrium iii gradients of 12% to 35% iodixanol and isolated.

Expression and Processing of DV2 mutants. Production and processing of DV2 host-range mutants was determined in *A. albopictus* C7-10 cells. Mosquito cells were infected with WT, DV2ΔGVII, and DV2ΔLIG and incubated at 28° C. for 1 week. Infected mosquito cell supernatants were then harvested and concentrated by tangential flow filtration (TFF) as per manufacturer's recommendations (PALL, Post Washington, N.Y.). Twenty-five μl of each preparation was loaded onto a 4-12% bis-tris gradient gel (Invitrogen). Proteins from the gel were transferred to a polyvinylidene difluoride membrane and blotted as described previously (Hernandez et al., 2001) with the following modifications: Primary anti-whole dengue virus mouse monoclonal antibody (Abeam #ab9202) was used for detection; an anti-mouse-HRP conjugate was used as a secondary antibody; and viral proteins were visualized by the addition of True-Blue™ peroxidise substrate (KPL).

RT-PCR analysis of mutant viruses. To confirm that the desired deletions remained intact in virus grown in cell culture, RNA was extracted from each mutant virus, reverse transcribed, and amplified by PCR (RT-PCR). RNA extraction was performed by two methods. The first method involved extracting RNA from a minimum of 104 ffu of virus by pelleting the virus at 50,000 rpm in a SW55Ti (Beckman Coulter, Brea, Calif.) rotor for 1 hour. The pelleted virus was extracted as described previously (Hernandez et al., 2000). The RNA pellet was resuspended in 10 μl of diethyl pyrocarbonate (DEPC) treated water and checked on 1% agarose gel. For smaller quantities of virus, a second method of purification was employed. Viral RNA was harvested from C6/36 cells by RNeasy Mini kit (Qiagen, Valencia, Calif.). Infected cells were scraped off flasks on Day 7 post-infection and suspended in media at a cell density of ~1×10$^7$ cells/ml. Cells were spun down, resuspended in lysis buffer, and homogenized. Viral RNA was purified as directed according to manufacturer's instructions. The resulting RNA was suspended in 30 μl of RNase free water and checked on a 1% agarose gel.

The extracted RNA was reverse transcribed and amplified by PCR using the One-Step RT-PCR kit (Qiagen). Primers were designed for use in the RT-PCR reaction by analysing the folded DV2 RNA structures to optimize RNA binding accessibility (Mathews et al., 1999). The products generated in the RT-PCR reaction (~640 bp) were phenol/chloroform extracted, precipitated and sequenced to confirm the identity and presence of deletions. Some of the RT-PCR products were of insufficient quantity and quality to be sequenced directly. These products were amplified by nested PCR, subcloned into the pDrive cloning vector and transformed in QIAGEN EZ Competent cells using the QIAGEN PCR cloningplus kit (Qiagen). White colonies containing the vector-ligated PCR product were amplified and the mini-preped DNA was sequenced for verification (Eurofins MWG Operon).

Focus reduction neutralization test (FRNT). The relative amount of virus-neutralizing antibody present in the mouse sera was determined by a focus reduction assay on Vero cells, which is similar to the standard Plaque Reduction Neutralization Test (WHO, 2009). The assay was performed as described above for the focus assay, with the addition of a pre-incubation step to allow serum antibody to bind WT DV2. In short, serum samples were heat inactivated for 30 minutes at 56° C. A dilution of 1:10 for each sample was prepared followed by serial 2-fold dilutions in dilution buffer containing 3% FBS. Each dilution was mixed with an equal volume of virus suspension containing 50 ffu of WT DV2 and incubated at 37° C. for 1 hour. 200 μl of the mixture was then added to duplicate wells seeded with Vero in a 24 well plate. After 1 hour of adsorption at 37° C., the cells were overlayed with 1× Vero media containing 1% CMC. At day 7 post-infection, antibody titers were determined by developing the plates according to the focus assay protocol. Neutralizing antibody titers (FRNT50) were reported as the highest dilution of the sera that reduced focus formation by 50%.

Experimental design for determination of neutralizing antibody titers. To evaluate DV2 specific neutralizing antibody responses, five groups (n=5) of 8 week old BALB/cJ mice were inoculated subcutaneously (SC) with 29 μg (~102-103 ffu/mouse) of the purified WT DV2, DV2ΔLIG, DV2ΔGVII, and iodixanol buffer alone. Protein estimates were made using the EZQC® Protein Quantitation Kit (Molecular Probes). Mice were boosted with an equal dose on Day 14 and serum samples were collected from all groups on Day 28, at the termination of the study. The relative amount of virus-neutralizing antibody present in mouse sera was determined by focus reduction neutralization test as described above (Mathews et al., 1999).

Transmission Electron Microscopy. Vero or C6/36 cells were transfected with RNA transcribed from WT DV2, DV2ΔLIG, or DV2ΔGVII clones. Incubation proceeded at 37° C. for 16-18 hours, after which the cell monolayers were scraped from the flasks and pelleted by low speed centrifugation. Cell pellets were washed twice with PBS and fixed with 3% glutaraldehyde (Ladd Research Industries, Inc., Williston, Vt.) in 0.1M cacodylic acid buffer pH 7.4 (Ladd Research Industries). After washing 3 times with 0.1M cacodylic acid, cells were stained with 2% osmium tetroxide in cacodylic buffer for 1 hour. Cells were then washed as before and embedded in 2% agarose. Agarose containing the cell sample was then pre-stained with 1% uranyl acetate (Polaron Instruments Inc., Hatfield, Pa.) overnight at 4° C. The samples were washed and carried through sequential dehydration with ethanol. Infiltration was achieved using SPURR compound (LADD Research Industries). Next blocks were trimmed on an LKB NOVA Ultrotome (Leica Microsystems, Inc., Deerfield, Ill.). Ultra-thin sections were obtained and stained with 5% uranyl acetate in distilled water for 60 minutes and in Reynolds lead citrate pH 12 (Mallinkrodt Baker Inc., Paris, Ky.) for 4 minutes. The samples were examined at 80 kV in a JEOL JEM 1005 transmission electron microscope.

EXAMPLE 2

Clinical Results Using Host Range Mutant Viruses as a Novel Dengue Virus-2 Vaccine To evaluate the immunogenicity, safety, and efficacy of a vaccine against DEN2, immunization experiments were performed in African green monkeys. African green monkeys provide a useful model for the preclinical assessment of novel candidates for Dengue vaccines (Martin et al., 2009a; Martin et al., 2009b).

Study design. In the present study, serum samples were collected and clinical observations made at baseline and at 1, 3, 5, 7, 14, 30 and 57 days after vaccine administration (Table 4). After serum collection on day 57 animals received live DEN-2 challenge virus (strain S16803 wild type; $10^5$ PFU per animal) before continued serum collection and clinical observations at 58-64, 71 and 142 days post-vaccine administration. All animals were prescreened for the presence of anti-Dengue1-4 IgM or IgG by ELISA. Monkeys positive by ELISA were excluded from the study.

TABLE 4

Study design

| Study day | Event | plasma volume (Cumulative vol.) |
|---|---|---|
| Day 0 | Blood sample for baseline dengue antibody Baseline PCV/Hematocrit (RxGEN) First vaccine dose | 5 ml (5 ml) |
| Day 1 | Animal observation (including injection site) Blood sample for vaccine viremia | 2 ml aliquot samples (7 ml) |
| Day 2 | Animal observation (including injection site) Blood Sample for vaccine viremia | 2 ml aliquot (9 ml) |
| Day 3 | Blood sample for vaccine viremia | 2 ml (11 ml) |
| Day 4 | Observation | — |
| Day 5 | Blood sample for IgM antibody, viremia | 2 ml (13 ml) |

TABLE 4-continued

Study design

| Study day | Event | plasma volume (Cumulative vol.) |
|---|---|---|
| Day 7 | Blood sample for IgM antibody, viremia | 2 ml (15 ml) |
| Day 14 | Blood sample for IgG antibody | 2 ml (17 ml) |
| Day 30 | Blood sample for IgG antibody PCV/Hematocrit (RxGEN) | 2 ml (19 ml) |
| Day 57 | Blood sample for IgG antibody PCV/Hematocrit (RxGEN) Virus Challenge | 2 ml (21 ml) |
| Day 58-64 | Blood samples collected for 7 consecutive days for WT challenge virus viremia measurement | 20 ml, 2 ml per day (41 ml) |
| Day 71 | Blood sample for IgG antibody | 2 ml (43 ml) |
| Day 142 | Blood sample for IgG antibody, study termination | 2 ml (45 ml) |
| | Total blood volume drawn (142 Study Days) | 45 ml |

It was determined that four monkeys per group (Table 5) would be sufficient to generate statistically significant data (Fisher's exact test P=0.05). The study design was based on previous studies done in the African Green Monkey model system (Martin et al., 2009a; Martin et al., 2009b) and rhesus monkeys (Halstead et al., 1973). No virus boost was incorporated because it was expected that the vaccine strains would generate sufficient viremia not to require a second dose. Cell supernatant from uninfected mosquito C6/36 cells was used as the negative control inoculum to monitor for the effect of mosquito antigens on the animals. The positive control used was the live attenuated (LAV) strain of DV2 S16803.

TABLE 5

Vaccine and Monkey Groups

| Group | Number of Animals | Dose 1 (Day 0) |
|---|---|---|
| 1 | 4 | Vaccine 1 (ΔGVII) 7.5 × $10^3$ ffu/monkey |
| 2 | 4 | Vaccine 2 (G460P) 7.5 × $10^4$ ffu/monkey |
| 3 | 4 | Vaccine 3 (ΔLIG) 2.5 × $10^3$ ffu/monkey |
| 4 | 4 | Negative control (cell filtrate with diluent) |
| 5 | 4 | Positive control (LAV) 5.0 × $10^5$ pfu/monkey |

Vaccines and challenge virus. Vaccine strains and the negative controls were administered in a total volume of 0.5 ml iodixanol solution (33% in PBS-D) after concentration by tangential flow filtration (TFF) and purification on 12% and 35% step iodixanol gradients to remove serum albumin and further concentrate the virus. Doses given of the host range mutant vaccine strains were as follows: DV2ΔLIG ($2.5×10^3$ ffu/monkey), DV2ΔGVII ($7.5×10^3$ ffu/monkey) and DV2G460P ($7.5×10^4$ ffu/monkey) (Table 5). The positive control (DV2 S16803 LAV) was administered in doses of $5.0×10^5$ pfu/monkey (Tables 5-6). Sequences of the mutagenized viruses and the control TMDs are shown in Table 6. All monkeys were challenged with DV2 516803 wild type virus at a dose of $1×10^3$ pfu/monkey (Table 6) (Eckels et al., 2003). DV2 516803 LAV passaged through PDK cells (Halstead and Marchette, 2003) and DV2 S16803 wild type virus were used as the control and challenge strains respectively because these strains have been extensively studied (Halstead et al., 1973; Marchette et al., 1973; Putnak et al., 2008). The response of monkey hosts to these DV2 S16803 LAV and wild type strains is well documented (Riedel and Brown, 1977; Sun et al., 2006; Vaughn et al., 1996).

A single vaccination with no boost was given via subcutaneous injection. The positive control, derivative LAV (strain 16803) was obtained from Robert Putnak of the WRAIR (Eckels et al., 2003). Table 6 shows the virus titers used for the wild-type and mutant viruses. Table 6 includes titers used for the following additional control strains: the DV216681 strain, which is the parent strain that was used to make the mutant ΔLIG and ΔGVII viruses, and the DV2S16803 strain, which is an attenuated LAV derivative strain that was also obtained from Robert Putnak of the WRAIR (Eckels et al., 2003).

TABLE 6

Virus titers for the DEN-2 WT virus and host range mutant viruses

| Virus | Strain | E-T1 Sequence | Titer (ffu/mL) Vero | C6/36 |
|---|---|---|---|---|
| WT DV2 | 16681 | SWTMKILIGVIITWIG (SEQ ID NO: 1) | $1 \times 10^6$ | $1 \times 10^7$ |
| DV2ΔLIG | 16681 | SWTMKI---VIITWIG (SEQ ID NO: 54) | $1 \times 10^1$ | $3 \times 10^4$ |
| DV2ΔGVII | 16681 | SWTMKILI----TWIG (SEQ ID NO: 55) | $1 \times 10^1$ | $4 \times 10^3$ |
| DV2G460P | 16681 | SWTMKILIPVIITWIG (SEQ ID NO: 56) | $2.5 \times 10^1$ | $5 \times 10^2$ |
| DV2LAV (attenuated) | 516803 | SWTMKILIGVIITWIG (SEQ ID NO: 1) | $1 \times 10^{4-5}$ | ND |
| DV2WT (wild-type) | 516803 | SWTMKILIGVIITWIG (SEQ ID NO: 1) | $1 \times 10^{4-5}$ | ND |

Figure 5:
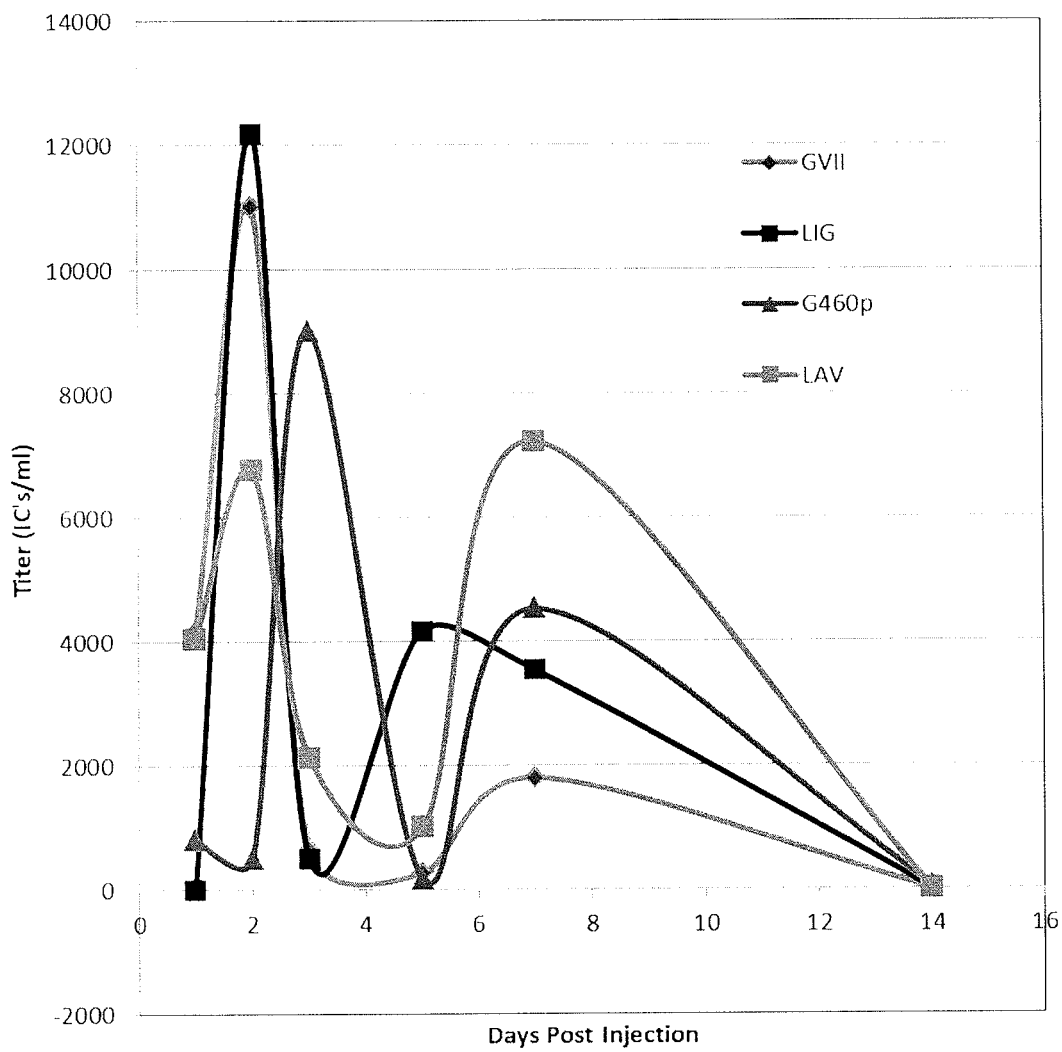
FIG. 5. Assessment of pre-challenge viremia in African green monkeys. Viremia analysis of serum samples from study day 1 through 14 was done by infectious center assay. The mock injected animals had no detectable viremia. The titers were plotted as average viremia titers for 4 monkeys/group.

Pre challenge viremia. Days 1, 2, 3, 5 and 7 post inoculation were chosen as the time points to assay for viremia in the monkey hosts. Viremia was found to peak on days 2-3 post injection for all test viruses. Shown in FIG. 5 is the peak viremia titer for the average of all 4 animals in each monkey group expressed as infectious centers/ml. The raw data (not presented) demonstrate that each individual monkey responded differently to the inoculation, although each group followed a notable trend. An assay of infectious centers (IC) was chosen over plaque assay since this assay is more sensitive by approximately 10 fold (data not presented) (Edwards and Brown, 1984; Putnak et al., 2005). The IC assay was also chosen to facilitate the isolation of individual IC to determine the sequence of the virus after replication in the primate host. This method of virus isolation made it possible to determine if reversion of the mutants was occurring during the viremia (see below). No viremia was detected in the mock infected controls. The amount of viremia detected in the test animals compares with the test vaccines reported in the literature (Missailidis and Brady, 2004) and compared to the control vaccine DV2 S16803 provided by Dr. Robert Putnak [Walter Reed Army Institute of Research (WRAIR)]. It is important to consider that while the control LAV injected at $10^5$ pfu/monkey produced a moderate level of viremia, an inoculum of $10^3$ total virus/500 μl in two of the test vaccines (ΔGVII and ΔLIG) produced equivalent virus titers in the host animals. This is significant because vaccine efficacy has been linked to viral load with lower dosages producing less protection (Simmons et al., 2006). This was not the case with the host range mutants in this study. Notably, viremia is seen in two distinct peaks, one at days 2-3 and a second between days 5 and 7. Distinct peaks of viremia have been detected in monkeys as well as humans. It is hypothesized that the first peak represents amplification of the virus in the sub-dermal dendritic cells in the epithelium at the site of injection (Libraty et al., 2001) with the infection progressing to a second site, possibly the draining lymph nodes (Cassetti et al., 2010). This type of dissemination of the virus has been seen in other test primates and in humans (Guy et al., 2009; Marchette et al., 1973; Martina et al., 2009). While the maximum titer of the two peaks of each of the viruses differs in quantity and day of onset, the total amount of virus for all vaccine strains days 1 through 14 is in the range of $10^4$ total IC/ml/monkey. These data demonstrate that the test vaccine strains did not produce more viremia in the test animals than the S16803 LAV control. These data are particularly important to demonstrate that the test vaccines are not more viremic than the well-established model DV2 LAV (Heegaard and Kennedy, 2002) and are indeed attenuated for replication in the animal host as proposed. Evaluation of IC from each virus group by sequence analysis has confirmed that ΔGVII virus from all four monkeys at day 2 had no reversions demonstrating the genetic stability of the largest deletion in the animal host.

No infectious centers were seen in the assay of serum from the mock infected animals.

Figure 6:
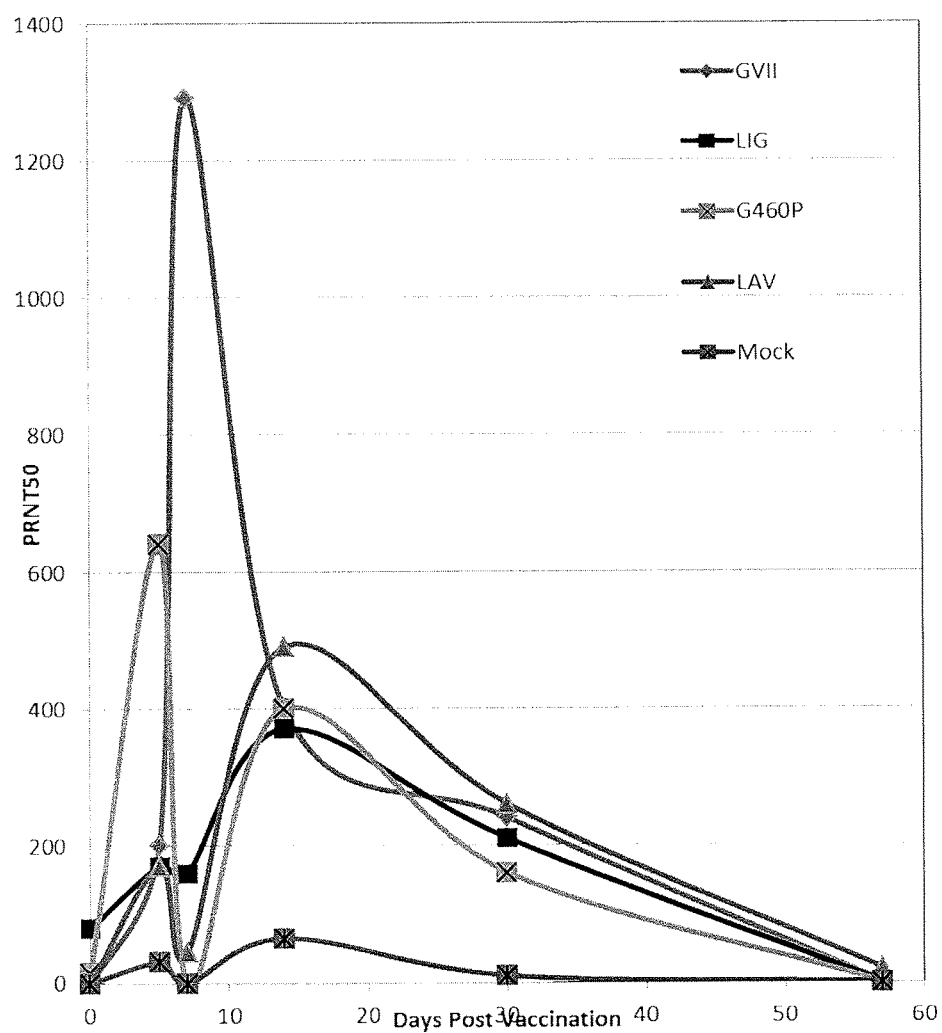
FIG. 6. Pre challenge NAb titers. The Nab titers were measured by Plaque Reduction Neutralization Test assay (PRNT) using the serum from each monkey per experimental group for Days 0, 5, 7, 14 and 30 post vaccination. Each data point represents the average of neutralizing antibody titers for all 4 monkeys per group.

Neutralizing Ab (NAb) data. Assay for the production of neutralizing IgM and IgG titers post vaccination began with day 5 post injection samples and included days 7, 14 and 30 (FIG. 6). Three different assays PRNT, FRNT and ELISA were used to test for Ab production and were performed on each individual sample in each group on the days reported. The average antibody titers from each group of animals are shown in FIG. 6. The numbers shown are from a plaque reduction neutralization assay (PRNT) and represent the inverse of the serum dilution in which 50% of the control DV2 virus was inhibited (Scott et al., 1983). Focus reduction neutralization assay (FRNT) was not as sensitive an assay. The monkeys were found to test positive for IgM on days 5, 7 and 14, with day 14 also beginning to show IgG. Only IgG was detected on day 30 which peaked at day 62 correlating well with the time course of virus neutralization (see FIG. 6 and FIGS. 9-10). These findings follow the progression for the production of IgM and IgG as seen in other test primates and humans (Velzing et al., 1999). As with the viremia raw data, the individual monkey Ab titers (not presented) demonstrate that each individual monkey responded differently to the inoculation, although each group followed notable trend. Ab production (pre-challenge) appears to peak on day 14 for the LAV strain (DV2 S16803) and the ΔLIG test vaccine strains. Mutant G460P peaked on days 5 and 14 while ΔGVII peaked on day 7. All strains showed neutralizing Ab titers on day 30 with the peak trailing to 0 at day 57. The control strain DV2 S16803 LAV produced NAb titers equivalent to those seen previously, ~500 $PRNT_{50}$/ml (Putnak et al., 1996). Compared to the control PRNT/50 titers, ΔGVII and G460P produced higher levels of NAb, in the 600 to 1300 $PRNT_{50}$/ml levels. As can be observed from FIG. 6, the levels of NAb are similar for all virus strains at day 14 which coincide with the end of the viremia (refer to FIG. 5).

Figure 7:
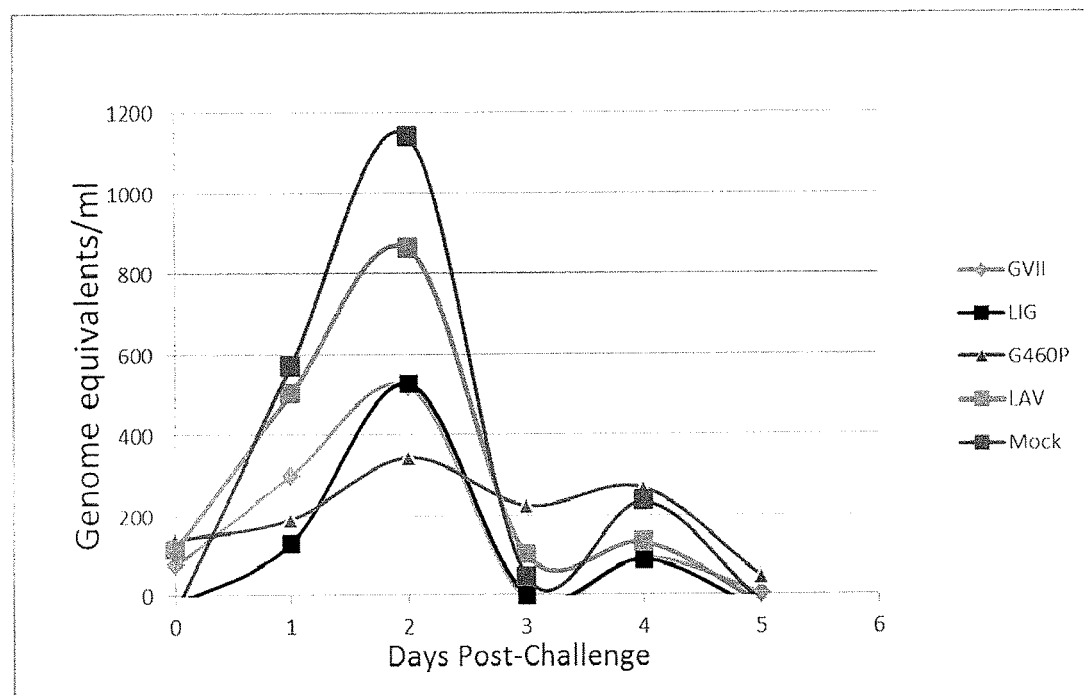
FIG. 7. Assessment of post-challenge viremia in African green monkeys. Monkeys were initially treated with a negative control, vaccine strain S16803 variant LAV, or the experimental DV2ΔLIG or DV2ΔGVII vaccine. On day 57, the monkeys were challenged with live DEN-2 challenge virus (strain S16803 wild type; 4-5 log 10 PFU per animal). The day 1 data point represents the first day post-challenge, which correlates with day 58 of the study. Each experimental group contained 4 monkeys, and the data points shown represent the average of the viremia measurements in genome equivalents/mL observed for all monkeys in each group.

Post Challenge viremia. Post challenge viremia and neutralizing Ab titers were determined for day 57 to 64 for 7 consecutive days. Data showing viremia after challenge are shown in FIG. 7. Plotted are the averages of the viremias assayed in all four monkeys of each of the vaccination groups determined by real time qRT-PCR (Bustin and Mueller, 2005) on days 1-5 post challenge. qRT-PCR was used because detection of virus by plaque assay cannot be used due to the high levels of NAb in the sera. All virus groups experienced viremia as measured in genome equivalents/ml with the mock vaccination group and the S16803 LAV control group producing the highest viremias. The test virus vaccines ΔGVII, G460P and ΔLIG allowed the least amount of virus replication/viremia of the challenge virus compared to the S16803 LAV control.

Figure 8:
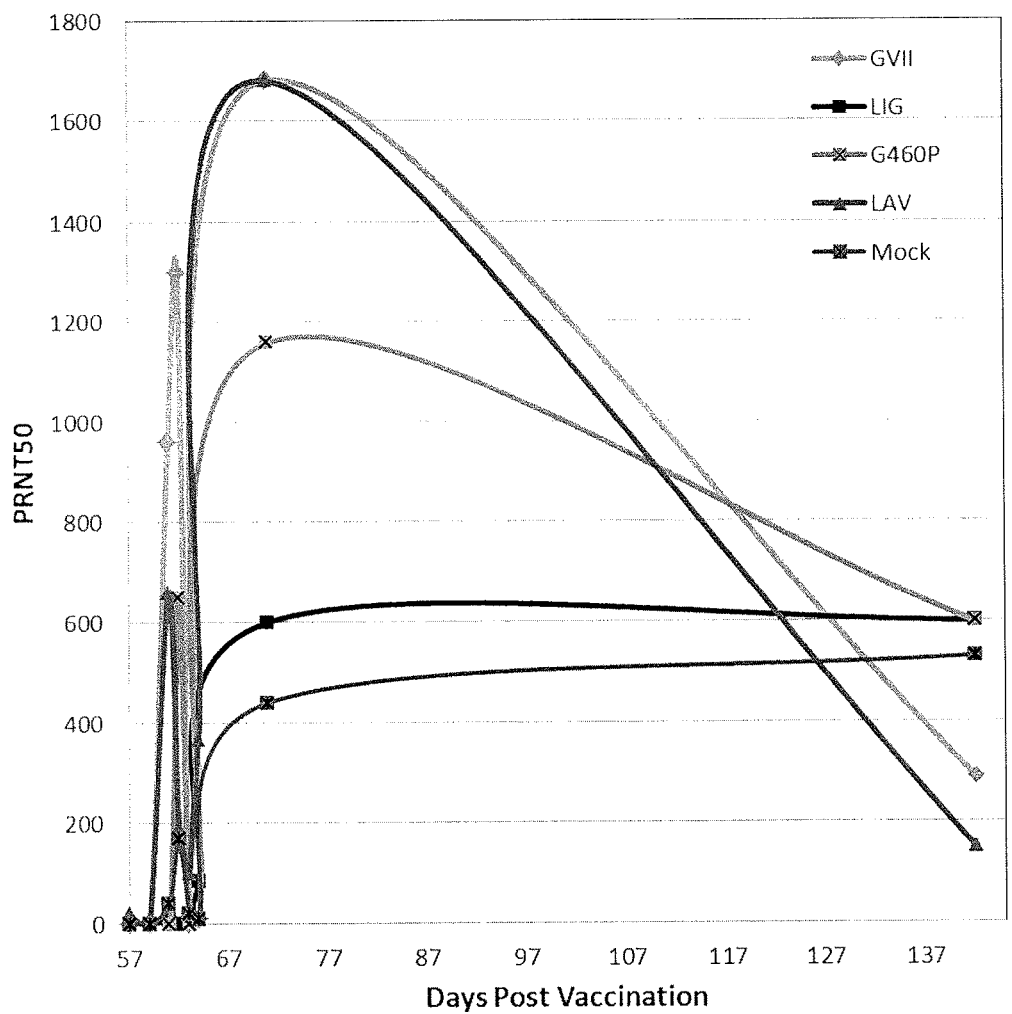
FIG. 8. Post-challenge Nab titers. The post-challenge Nab titers were measured by PRNT using the serum from each monkey per experimental group for Days 57, 59, 61, 62, 63, 64, 71 and 142 post vaccination. Each data point represents the average of neutralizing antibody titers for all 4 monkeys per group.

Pre and Post Challenge Neutralizing Ab data. Assay of neutralizing Ab titers after challenge began at day 57 post inoculation and continued for 7 consecutive days, sampled again at day 71 with a terminal blood draw taken at day 142. Results from the PRNT tests are shown in FIG. 8. NAb begins to appear again on day 4 post challenge. With the exception of ΔLIG, which peaks at day 71, all virus strains show a peak of NAb on day 61 or 62 which drops through day 63 and begins to increase again on day 71. Maximal values of NAb titer, including those seen for ΔLIG were seen at day 71 post vaccination and are similar in their time course to the NAb response in the initial post vaccination period (FIG. 5). All vaccine strains tested elicited a neutralizing response above 1:300 $PRNT_{50}$ titer by day 71 post challenge. The bimodal peaks of neutralization produced after challenge were unexpected but were reproducible. Additionally the bimodal peaks of IgG Ab were also detected in the ELISA assay suggesting that there was a real drop in IgG titer on day 63 post vaccination. Because this peak also occurred in the mock vaccinated monkeys, it is possible that this response was due to some component of the challenge inoculum. Whatever the cause, Nab titers returned to high levels at day 71 post vaccination. The plaque reduction neutralization tests completed for the post challenge virus samples demonstrate that the levels of NAb detected for ΔGVII and G460P exceeded the Ab titers produced by the control virus LAV S16803 based on the quantity of virus injected (see Table 5).

Figure 9:
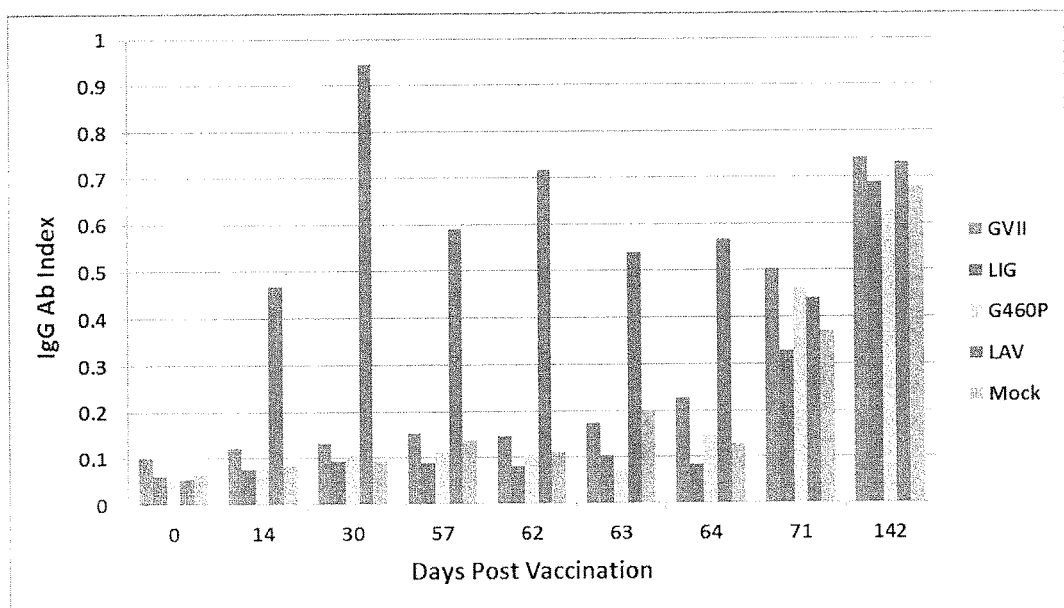
FIG. 9. Total IgG pre and post challenge. Total IgG was measured by Dengue IgG ELISA kit. Each bar represents the average Antibody Index of 4 monkey serum samples per experimental group. The measurements were done on the days represented on X-axis.
Figure 10:
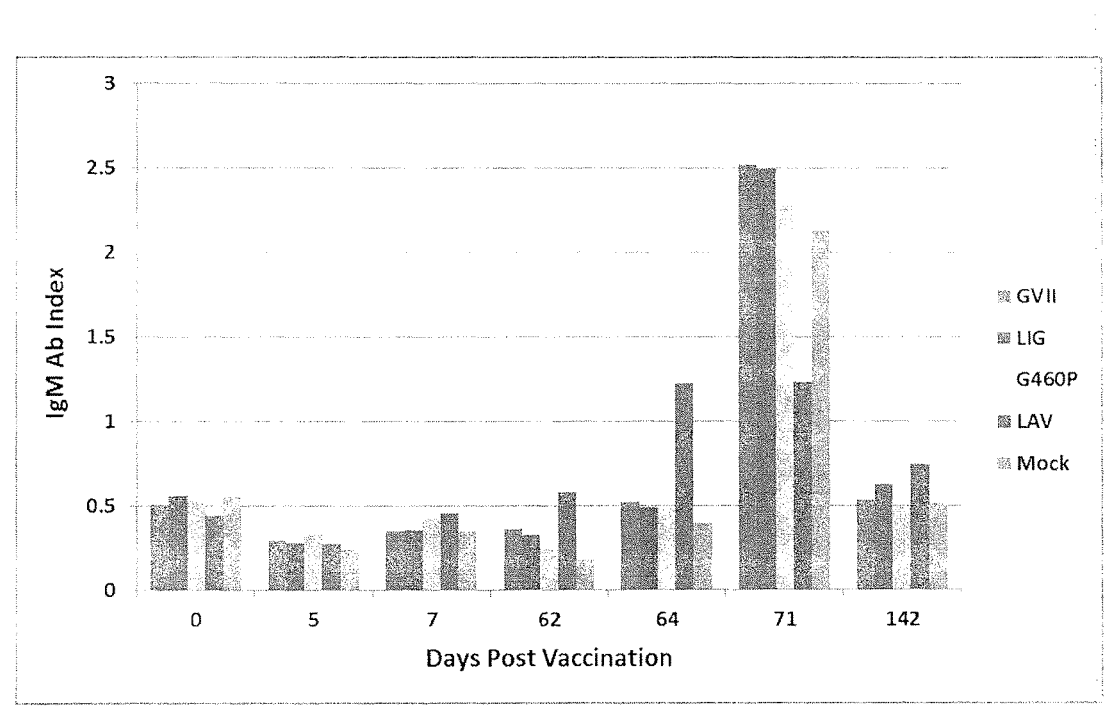

Total Ab, pre and post virus challenge. The Ab types elicited during the virus neutralization response were determined by ELISA to be both IgM and IgG. This suggests that both IgG and IgM may contribute to the neutralizing activity because the levels of both Abs followed the trends for NAb seen in the $PRNT_{50}$ assays. Shown in FIG. 9 are the total IgG indices for each of the virus groups' pre and post challenge. There was no peak of IgM detected at day 61-62 post challenge, rather IgM peaked at day 71 post challenge (FIG. 10) NAb levels which peaked on day 71 post vaccination declined at day 142 in the ΔGVII, G460P and LAV samples, while ΔLIG and the mock samples plateaued. At a $PRNT_{5U}$ level of 600 units, the amount of NAb for ΔLIG and G460P were still high as was the challenged mock. Total IgG against all mutant viruses tested peaked at the end of the study at day 142 while IgM levels declined. Comparison of the IgG and IgM levels suggests that IgM levels were elicited after IgG as has been reported previously to occur after virus challenge (Bernardo et al., 2008; WHO, 2006). It was unexpected to find that the total IgG levels against the LAV control virus were so much higher than the test or control serum samples through day 142 post vaccination. This suggests that the amount of total IgG against LAV must be largely non-neutralizing because the NAb titers for the mutant and LAV vaccine strains were similar or larger in magnitude during the post vaccination period. By day 142 the levels of neutralization are declining for LAV and ΔGVII while ΔLIG, G460P and the challenge DV2 S16803 levels remain high. NAb titers at maintenance levels were not determined since no additional blood draws were taken past 142 days.

Safety assessment. Data generated in this Example was designed to assess efficacy, immunogenicity and safety in African green monkeys to support preclinical validation of novel candidate dengue vaccines. Safety was assessed by clinical observations performed from baseline until completion of in vivo studies on study day 71 (extended to day 142) as well as determination of complete blood cell counts (CBCs) at baseline and on study days 30 and 57. No major clinical concerns related to experimental vaccines were identified as part of performed assessments. No erythema was observed at injection sites and no fever was observed in the days following experimental vaccine administration.

Figure 11:
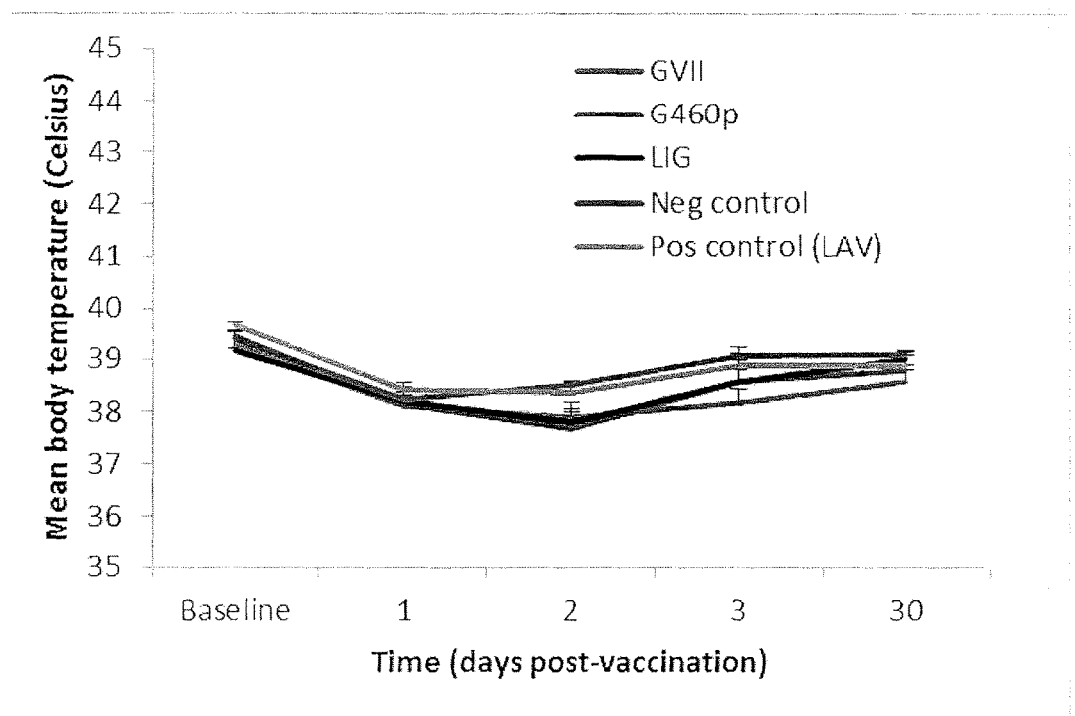
FIG. 11. Changes in body temperature following vaccine administration. Body temperature was determined using a rectal thermometer as part of clinical observations. Data points indicate the mean body temperature with vertical bars representing the standard error, SEM (n=4). The body temperatures were measured on the days 0, 1, 2, 3 and 30 after vaccination.

Twenty monkeys were assigned to one of five treatment groups to evaluate viremia and antibody responses to test vaccine delivery and subsequent challenge with live virus. Clinical observations were made over the initial 3 days following vaccine delivery and again after the viral challenges were performed in the same animals. No increases in body temperatures were observed following subcutaneous delivery of experimental vaccines (ΔGVII, G460P or ΔLIG) or administration of LAV or the negative control (FIG. 11). Similarly, no major changes in heart rate or respiratory rate were observed as a result of experimental vaccine administration compared to control groups (data not presented).

Body temperature was determined using a rectal thermometer as part of clinical observations. Data points indicate the mean body temperature with vertical bars representing the standard error, SEM (n=4).

Figure 12:
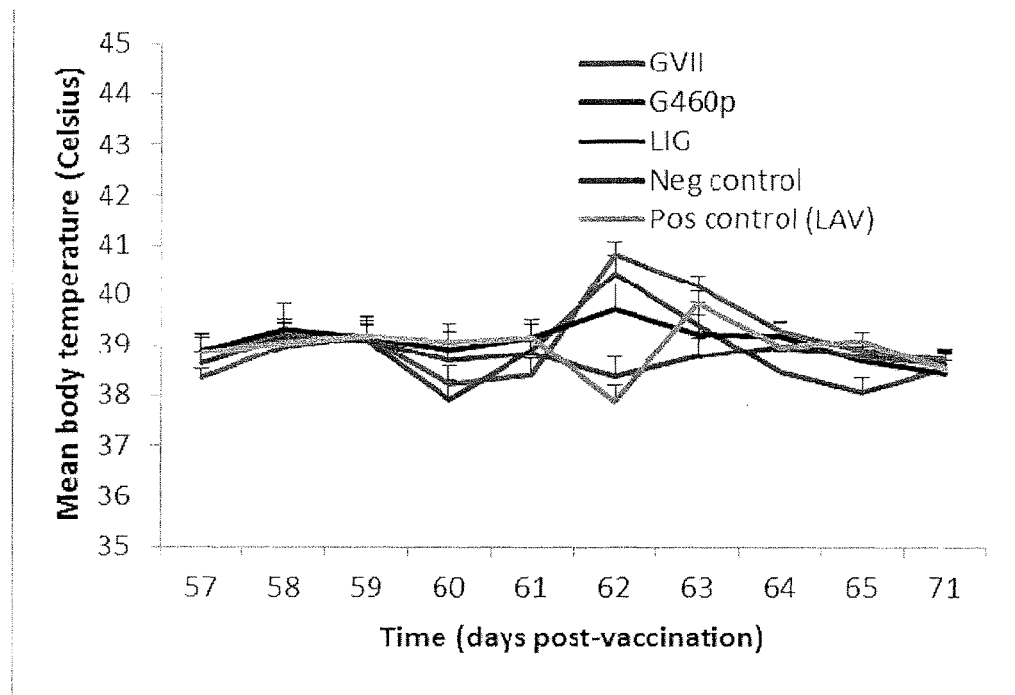
FIG. 12. Changes in body temperature following viral challenge. Body temperature was determined using a rectal thermometer as part of clinical observations. Data points indicate the mean body temperatures with vertical bars representing the standard error, SEM (n+4). The body temperatures were measured on the day 57 through 65 and on day 71 post vaccination.

Clinical observations made after viral challenge at day 57 highlighted modest but significant differences between treatment groups. Minimal body temperature increases were observed in the initial 4 days following viral challenge across all treatment groups. On day 62 (5 days post-viral challenge) a significant spike in temperatures was observed for animals that had received ΔGVII and G460P vaccines (FIG. 12). Body temperatures steadily declined towards baseline levels over the next 2-3 days with no other clinical abnormalities observed during this time. This spike in temperature was preceded by viremia at day 58 and followed by the second spike in NAb by one to three days (63 and 64). Analysis of the data suggests that these small spikes are not significantly different from that seen in the LAV control at day 7. Minor changes in specific CBC measures were noted but these changes, which included reduced platelet counts, were not consistent with a vaccine-specific safety concern as similar findings were observed in control groups.

Body temperature was determined using a rectal thermometer as part of clinical observations. Data points indicate the mean body temperature with vertical bars representing the SEM (n=4).

CONCLUSIONS

Administration of experimental vaccines produced no significant safety concerns with no evidence of injection site erythema and no evidence of fever following subcutaneous delivery. No pyrexia or other clinical signs were observed following administration of experimental vaccines, positive (LAY) or negative controls.

Dengue infection in African green monkeys demonstrated similar absence of pyrexia following live dengue serotype-2 infection (Martin et al., 2009a; Martin et al., 2009b). Interestingly, following subsequent viral challenge at 57 days post-vaccine delivery a brief spike in body temperature was observed in animals receiving ΔGVII and G460P experimental vaccines and to some extent in LAV but not in any other treatment groups suggesting differing responses to infection in these treatment groups. It is of particular interest to assess whether observed body temperature changes following viral challenge reflect any differences in immunogenicity and efficacy as a result of vaccine treatment. Indeed, this was not found to be the case because all three test vaccines displayed high efficacy in suppressing the challenge virus viremia. Of the three host range vaccine strains tested post challenge virus NAb levels elicited were shown to be GVII>G460P>LIG as compared to the LAV control. All vaccine candidates gave NAb levels of >320 $PRNT_{50}$ values. A minimal sero-conversion $PRNT_{50}$ value of 10 or greater is generally accepted which puts these values into the high responding NAb category (Russell et al., 1967). All test vaccines were able to protect monkeys from viremia to a greater extent than the LAV vaccine control.

Overall, with the endpoints assessed in the present studies no significant safety concerns were identified that would adversely impact continued preclinical development. One or more of the test vaccines would be efficacious and immunogenic for clinical applications. More detailed analysis of CBC data may provide more information on the immune response of these monkeys to the vaccine strains tested. In conjunction with viremia and antibody response results these data have provided great insights into the safety and efficacy of these test viruses. This initial study provides evidence that all mutants tested appeared safe, producing no significant side effects. All three vaccine strains tested were efficacious in reducing the amount of viremia upon WT DV2 16803 challenge. All three candidates also were found to induce an excellent neutralizing immune response compared to the LAV control. One important observation is that all three test vaccine strains elicited much less non neutralizing IgG than the LAV control. This is a significant finding because it is thought that non neutralizing Ab contributes to the Ab dependent enhancement leading to the abnormal immune response resulting in hemorrhagic disease (Halstead et al., 1977; Huang et al., 2006; Littaua et al., 1990). These tests and data support the development of similar vaccine strains in DV 1, 3 and 4 which will be poised to continue development either singly or in combination to enter phase 1 clinical trials.

* * *

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,791,932
U.S. Pat. No. 3,949,064
U.S. Pat. No. 4,174,384
Adams and Rose, *Cell*, 41(3):1007-1015, 1985.
Amberg et al., *J. Virol.*, 73:8083-8094, 1999.
Bernardo et al., *Arch. Virology*, 153:849-854, 2008.
Bowers et al., *Virology*, 212(1):1-12, 1995.
Bretscher and Munro, *Science*, 261:1280-1, 1993.
Brown and Condreay, In: *The Togaviruses and Flavivirdae*. Schlesinger et al. (Eds.), 11(2/3):225-237, Plenum Press, NY, 1986.
Bustin and Mueller, *Clin. Sci. (Lond)*, 109:365-79, 2005.
Cassetti et al., *Vaccine*, 28:4229-34, 2010.
Clayton, *J. Lipid. Res.*, 15:3-19, 1964.
Condreay and Brown, *J. Virol.*, 58:81-6, 1986.
Eckels et al., *Am. J. Trop. Med. Hyg.*, 69:12-16, 2003.
Eckels, et al., *Am. J. Trop. Med. Hyg.*, 69:12-16, 2003
Edwards and Brown, *Virology*, 182(1):28-33, 1991.
Edwards and Brown, *Virus Res.*, 1:703-711, 1984.
Gresikova et al., In: *The Arboviruses, Ecology and Epidemiology*, Monath (Ed.), CRC Press, Boca Raton, Fla., IV:177-203, 1988.
Guy et al., *Am. J. Trop. Med. Hyg.*, 80:302-11, 2009.
Halstead and Marchette, *Am. J. Trop. Med. Hyg.*, 69:5-11, 2003.
Halstead et al., *J. Exp. Med.*, 146:218-29, 1977.
Halstead et al., *J. Infect. Dis.*, 128:15-22, 1973
Heegaard and Kennedy, *J. Chromatogr. B Analyt. Technol. Biomed. Life Sci.*, 768:93-103, 2002.
Hernandez et al., *Curr. Protoc. Microbiol.*, 15:15 B-1, 2005.
Hernandez et al. *J. Virol.*, 74:4220-8, 2000.
Hernandez et al., *J. Virol.*, 75:2010-3, 2001.
Hernandez et al., *J. Virol.*, 77(23):12710-9, 2003.
Huang et al., *J. Immunol.*, 176:2825-2832, 2006.
Irie et al., *Gene*, 75:197-211, 1989.
Klaassen, In: *The Pharmacological Basis of Therapeutics*, Goodman and Gilman (Eds.), Pergamon Press, $8^{th}$ Ed., 1990.
Libraty et al., *J. Virol.*, 75:3501-8, 2001.
Littaua et al., *J. Immunol.*, 144:3183-3186, 1990.
Lobigs and Lee, *J. Virol.*, 78:178-86, 2004.
Lobigs et al., *Immunol. Cell Biol.*, 82:184-8, 2004.
Marchette et al., *J. Infect. Dis.*, 128:23-30, 1973.
Martin et al., *Curr. Microbiol.*, 59:579-83, 2009a.
Martin et al., *Microbiol. Immunol.*, 53:216-23, 2009b.
Martina et al., *Clin. Microbiol. Rev.*, 22:564-581, 2009.

Mathews et al., *J. Mol. Biol.*, 288:911-40, 1999.
Missailidis and Brady, *Methods Mol. Biol.*, 248:431-41, 2004.
Mitsuhashi et al., *Cell Biol. Int. Rep.*, 7(12):1057-62, 1983.
Monath, In: *The Togaviridae and Flaviviridae*, Schlesinger et al. (Eds.), 375-440, Plenum Press, NY, 1986.
Morens et al., *J. Clin. Microbiol.*, (2):250-254, 1985.
Mukhopadhyay et al., *Nat. Rev. Microbiol.*, 3:13-22, 2005.
Murray et al., *Nat. Rev. Micro.*, 6:699-708, 2008.
Putnak et al., *Am. J. Trop. Med. Hyg.*, 79:115-22, 2008.
Putnak et al., *J. Infect. Dis.*, 174:1176-84., 1996
Putnak et al., *Vaccine*, 23:4442-52, 2005.
Remington's Pharmaceutical Sciences, 18th Ed. Mack Printing Company, 1990.
Renz and Brown, *J. Virol.*, 19:775-81, 1976.
Rice et al., *J. Clin. Invest.*, 70(1):157-67, 1982.
Rice, In: *Virology*, Fields (Ed.), Raven-Lippincott, NY, 1:937, 1995.
Riedel and Brown, *J. Virol.*, 23:554-61, 1977.
Rost et al., *Nucl. Acids Res.*, 32:W321-326, 2004.
Russell, et al., *J. Immunol.*, 99:285-290, 1967.
Sambrook et al., In: *Molecular Cloning: a Laboratory Manual*, 2$^{nd}$ Ed., Cold Spring Harbor Laboratory Press, Cold Spring Harbor, N.Y., 1987.
Samsa et al., *PLoS Pathog.*, 5:e1000632, 2009.
Schlesinger and, Schlesinger, In: *Virology*, 2$^{nd}$ Ed., Fields et al. (Ed.), Raven Press, NY, 697-712, 1990.
Schmaljohn et al., *Nature*, 297(5860:70-2, 1982.
Schmaljohn et al., *Virology*, 130(1):144-54, 1983.
Scott et al., *J. Infect. Dis.*, 148:1055-1060, 1983.
Simmons et al., *Virology*, 396:280-8, 2006.
Sun et al., *J. Infect. Dis.*, 193:1658-65, 2006.
Vaughn et al., *Vaccine*, 14:329-36, 1996.
Velzing et al., *Vaccine*, 17:1312-1320, 1999.
West et al. *J. Virol.*, 80:4458-68, 2006.
WHO, Report of the meeting of the WHO Task Force on Clinical Trials of Dengue Vaccines, 2006.
WHO, Dengue haemorrhagic fever: diagnosis, treatment prevention and control-2$^{nd}$ Ed., Geneva, 1997.
WHO, W.H.O. *Vector-borne viral infections*, 2009.
Zhang et al., *Nat. Struct. Biol.*, 10:907-12, 2003.

What is claimed is:

1. A modified flavivirus envelope (E) protein comprising a mutated E protein's N-terminal transmembrane domain (E-T1 domain), such a mutation comprising a deletion of amino acids at positions of 0 to +3, 0 to +4, −2 to 0, −3 to 0, or −1 to +1, wherein the unmodified E-T1 domain comprises a central glycine amino acid and the deletion is relative to said central glycine, which is designated as position 0, and wherein the mutation selectively inhibits the replication of a flavivirus comprising the modified flavivirus E protein in mammalian cells relative to insect cells.

2. The modified flavivirus envelope protein of claim 1, wherein the mutation comprises a deletion of amino acids at positions of 0 to +3 relative to the central glycine amino acid.

3. The modified flavivirus envelope protein of claim 1, wherein the mutation comprises a deletion of amino acids at positions of −2 to 0 relative to the central glycine amino acid.

4. The modified flavivirus envelope protein of claim 1, wherein the modified flavivirus E protein is a modified E protein of Dengue virus (DV), West Nile virus (WNV), yellow fever virus (YFV), Japanese encephalitis virus (JEV), tick-borne encephalitis virus (TBE virus), Murray Valley encephalitis virus (MVEV), Saint Louis encephalitis virus (SLEV), or Powassan virus (PV).

5. The modified flavivirus envelope protein of claim 4, wherein the modified flavivirus E protein is a modified E protein of Dengue virus.

6. The modified flavivirus envelope protein of claim 5, wherein the modified flavivirus E protein is a modified E protein of Dengue virus type 2.

7. The modified flavivirus envelope protein of claim 6, wherein the mutation comprises a deletion at L458 to G460.

8. The modified flavivirus envelope protein of claim 6, wherein the mutation comprises a deletion at amino acids G460 to I463.

9. The modified flavivirus envelope protein of claim 1, wherein a virus comprising the modified flavivirus E protein has an ability to produce at least 100 fold more progeny viruses when infecting insect cells than when infecting mammalian cells.

10. The modified flavivirus envelope protein of claim 9, wherein a virus comprising the modified flavivirus E protein has an ability to produce at least 1000 fold more progeny viruses when infecting insect cells than when infecting mammalian cells.

11. An engineered nucleic acid encoding a modified flavivirus envelop protein of claim 1.

12. A genetically engineered flavivirus comprising at least an engineered nucleic acid of claim 11.

13. An immunogenic composition comprising a genetically engineered flavivirus of claim 12.

14. The immunogenic composition of claim 13, further defined as a vaccine composition.

15. The immunogenic composition of claim 14, wherein the vaccine composition comprises one or more of the genetically engineered Dengue virus types 1, 2, 3, and 4.

16. The immunogenic composition of claim 15, wherein the vaccine composition comprises the genetically engineered Dengue virus type 2.

17. The immunogenic composition of claim 15, wherein the vaccine composition is a tetravalent vaccine composition comprising the genetically engineered Dengue virus types 1, 2, 3, and 4.

18. The immunogenic composition of claim 13, further comprising an adjuvant or a preservative.

19. A method of producing a viral vaccine for vaccination of mammals, comprising introducing the genetically engineered flavivirus of claim 12 to insect cells to produce a viral vaccine.

20. A method of inducing an immune response in a mammal, comprising administering the immunogenic composition of claim 13 to the mammal.

21. A method of vaccinating a mammal, comprising administering the vaccine composition of claim 14 to a mammal.

22. The method of claim 21, wherein the mammal is a human or a primate.

23. The method of claim 21, wherein the administration is intravenous, intramuscular, intraperitoneal or subcutaneous.

24. The method of claim 21, wherein the administration is a single-dose administration.

* * * * *

```
                        SEQUENCE LISTING

<160> NUMBER OF SEQ ID NOS: 56

<210> SEQ ID NO 1
<211> LENGTH: 16
<212> TYPE: PRT
<213> ORGANISM: Artificial Sequence
<220> FEATURE:
<223> OTHER INFORMATION: Synthetic peptide

<400> SEQUENCE: 1

Ser Trp Thr Met Lys Ile Leu Ile Gly Val Ile Ile Thr Trp Ile Gly
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Synthetic peptide

<400> SEQUENCE: 2

Ser Trp Leu Ser Arg Leu Met Ile Gly Ala Leu Cys Leu Trp Ile Gly
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Synthetic peptide

<400> SEQUENCE: 3

Ser Trp Ile Thr Gln Gly Leu Leu Gly Ala Leu Leu Leu Trp Met Gly
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Synthetic peptide

<400> SEQUENCE: 4

Asn Trp Ile Val Lys Ile Leu Ile Gly Thr Ile Phe Leu Trp Leu Gly
1               5                   10                  15
```

```
<210> SEQ ID NO 5
<211> LENGTH: 16
<212> TYPE: PRT
<213> ORGANISM: Artificial Sequence
<220> FEATURE:
<223> OTHER INFORMATION: Synthetic peptide

<400> SEQUENCE: 5

Ser Trp Ile Thr Gln Gly Leu Met Gly Ala Leu Leu Leu Trp Met Gly
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Synthetic peptide

<400> SEQUENCE: 6

Gly Phe Met Met Lys Met Ile Ile Ser Leu Val Leu Ile Trp Phe Cys
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Synthetic peptide

<400> SEQUENCE: 7

Ser Trp Ile Ser Pro Gly Leu Leu Gly Ala Leu Leu Leu Trp Met Gly
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Synthetic peptide

<400> SEQUENCE: 8

Gly Phe Leu Pro Arg Ile Leu Leu Gly Ile Ser Leu Ala Trp Leu Gly
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Synthetic peptide

<400> SEQUENCE: 9

Gly Phe Leu Gly Lys Leu Met Ile Ser Gly Val Leu Ile Trp Leu Cys
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Synthetic peptide

<400> SEQUENCE: 10

Ser Trp Ile Thr Gln Gly Leu Leu Gly Ala Leu Leu Leu Trp Met Gly
1               5                   10                  15
```

```
<210> SEQ ID NO 11
<211> LENGTH: 16
<212> TYPE: PRT
<213> ORGANISM: Artificial Sequence
<220> FEATURE:
<223> OTHER INFORMATION: Synthetic peptide

<400> SEQUENCE: 11

Gly Phe Leu Pro Lys Leu Leu Leu Gly Val Ala Leu Ala Trp Leu Gly
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Synthetic peptide

<400> SEQUENCE: 12

Ser Trp Ile Thr Gln Gly Leu Leu Gly Ala Leu Leu Leu Trp Met Gly
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Synthetic peptide

<400> SEQUENCE: 13

Asn Trp Ile Thr Lys Val Ile Met Gly Ala Val Leu Ile Trp Val Gly
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Synthetic peptide

<400> SEQUENCE: 14

Ser Trp Phe Ser Gln Ile Leu Ile Gly Thr Leu Leu Val Trp Leu Gly
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Synthetic peptide

<400> SEQUENCE: 15

Ser Trp Thr Met Lys Ile Gly Ile Gly Ile Leu Leu Thr Trp Leu Gly
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Synthetic peptide

<400> SEQUENCE: 16

Ser Trp Ile Met Lys Ile Gly Ile Gly Val Leu Leu Thr Trp Ile Gly
1               5                   10                  15
```

```
<210> SEQ ID NO 17
<211> LENGTH: 16
<212> TYPE: PRT
<213> ORGANISM: Artificial Sequence
<220> FEATURE:
<223> OTHER INFORMATION: Synthetic peptide

<400> SEQUENCE: 17

Ser Trp Met Ile Arg Ile Leu Ile Gly Phe Leu Val Leu Trp Ile Gly
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Synthetic peptide

<400> SEQUENCE: 18

Ser Trp Ile Thr Gln Gly Leu Leu Gly Ala Leu Leu Leu Trp Met Gly
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic peptide

<400> SEQUENCE: 19

Ser Trp Thr Met Lys Ile Leu Ile Gly Val Ile Thr Trp Ile Gly
1               5                   10                  15

<210> SEQ ID NO 20
<211> LENGTH: 14
<212> TYPE: PRT
<213> ORGANISM: Artificial Sequence
<220> FEATURE:
<223> OTHER INFORMATION: Synthetic peptide

<400> SEQUENCE: 20

Ser Trp Thr Met Lys Ile Leu Ile Gly Val Thr Trp Ile Gly
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Synthetic peptide

<400> SEQUENCE: 21

Ser Trp Thr Met Lys Ile Leu Ile Gly Thr Trp Ile Gly
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic peptide

<400> SEQUENCE: 22

Ser Trp Thr Met Lys Ile Leu Ile Thr Trp Ile Gly
1               5                   10
```

```
<210> SEQ ID NO 23
<211> LENGTH: 11
<212> TYPE: PRT
<213> ORGANISM: Artificial Sequence
<220> FEATURE:
<223> OTHER INFORMATION: Synthetic peptide

<400> SEQUENCE: 23

Ser Trp Thr Met Lys Ile Leu Ile Trp Ile Gly
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Synthetic peptide

<400> SEQUENCE: 24

Ser Trp Thr Met Lys Ile Leu Thr Trp Ile Gly
1               5                   10

<210> SEQ ID NO 25
<211> LENGTH: 15
<212> TYPE: PRT
<213> ORGANISM: Artificial Sequence
<220> FEATURE:
<223> OTHER INFORMATION: Synthetic peptide

<400> SEQUENCE: 25

Ser Trp Thr Met Lys Ile Leu Ile Val Ile Ile Thr Trp Ile Gly
1               5                   10                  15

<210> SEQ ID NO 26
<211> LENGTH: 14
<212> TYPE: PRT
<213> ORGANISM: Artificial Sequence
<220> FEATURE:
<223> OTHER INFORMATION: Synthetic peptide

<400> SEQUENCE: 26

Ser Trp Thr Met Lys Ile Leu Val Ile Ile Thr Trp Ile Gly
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Synthetic peptide

<400> SEQUENCE: 27

Ser Trp Thr Met Lys Ile Val Ile Ile Thr Trp Ile Gly
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Synthetic peptide

<400> SEQUENCE: 28

Ser Trp Thr Met Lys Val Ile Ile Thr Trp Ile Gly
1               5                   10
```

```
<210> SEQ ID NO 29
<211> LENGTH: 11
<212> TYPE: PRT
<213> ORGANISM: Artificial Sequence
<220> FEATURE:
<223> OTHER INFORMATION: Synthetic peptide

<400> SEQUENCE: 29

Ser Trp Thr Met Lys Ile Ile Thr Trp Ile Gly
1               5                   10

<210> SEQ ID NO 30
<211> LENGTH: 15
<212> TYPE: PRT
<213> ORGANISM: Artificial Sequence
<220> FEATURE:
<223> OTHER INFORMATION: Synthetic peptide

<400> SEQUENCE: 30

Ser Trp Thr Met Ile Leu Ile Gly Val Ile Ile Thr Trp Ile Gly
1               5                   10                  15

<210> SEQ ID NO 31
<211> LENGTH: 14
<212> TYPE: PRT
<213> ORGANISM: Artificial Sequence
<220> FEATURE:
<223> OTHER INFORMATION: Synthetic peptide

<400> SEQUENCE: 31

Ser Trp Thr Ile Leu Ile Gly Val Ile Ile Thr Trp Ile Gly
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Synthetic peptide

<400> SEQUENCE: 32

Ser Trp Lys Ile Leu Ile Gly Val Ile Ile Thr Trp Ile Gly
1               5                   10

<210> SEQ ID NO 33
<211> LENGTH: 15
<212> TYPE: PRT
<213> ORGANISM: Artificial Sequence
<220> FEATURE:
<223> OTHER INFORMATION: Synthetic peptide

<400> SEQUENCE: 33

Ser Trp Thr Met Lys Ile Leu Ile Gly Val Ile Ile Trp Ile Gly
1               5                   10                  15

<210> SEQ ID NO 34
<211> LENGTH: 14
<212> TYPE: PRT
<213> ORGANISM: Artificial Sequence
<220> FEATURE:
<223> OTHER INFORMATION: Synthetic peptide

<400> SEQUENCE: 34

Ser Trp Thr Met Lys Ile Leu Ile Gly Val Ile Trp Ile Gly
1               5                   10
```

```
<210> SEQ ID NO 35
<211> LENGTH: 13
<212> TYPE: PRT
<213> ORGANISM: Artificial Sequence
<220> FEATURE:
<223> OTHER INFORMATION: Synthetic peptide

<400> SEQUENCE: 35

Ser Trp Thr Met Lys Ile Leu Ile Gly Val Trp Ile Gly
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Synthetic peptide

<400> SEQUENCE: 36

Ser Trp Thr Met Lys Ile Leu Ile Gly Trp Ile Gly
1               5                   10

<210> SEQ ID NO 37
<211> LENGTH: 15
<212> TYPE: PRT
<213> ORGANISM: Artificial Sequence
<220> FEATURE:
<223> OTHER INFORMATION: Synthetic peptide

<400> SEQUENCE: 37

Ser Trp Thr Met Lys Ile Leu Ile Gly Ile Ile Thr Trp Ile Gly
1               5                   10                  15

<210> SEQ ID NO 38
<211> LENGTH: 14
<212> TYPE: PRT
<213> ORGANISM: Artificial Sequence
<220> FEATURE:
<223> OTHER INFORMATION: Synthetic peptide

<400> SEQUENCE: 38

Ser Trp Thr Met Lys Ile Leu Ile Ile Ile Thr Trp Ile Gly
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Synthetic peptide

<400> SEQUENCE: 39

Ser Trp Thr Met Lys Ile Leu Ile Ile Thr Trp Ile Gly
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Synthetic peptide

<400> SEQUENCE: 40

Ser Trp Thr Met Lys Ile Leu Ile Ile Thr Trp Ile Gly
1               5                   10
```

-continued

```
<210> SEQ ID NO 41
<211> LENGTH: 14
<212> TYPE: PRT
<213> ORGANISM: Artificial Sequence
<220> FEATURE:
<223> OTHER INFORMATION: Synthetic peptide

<400> SEQUENCE: 41

Ser Trp Thr Met Lys Ile Leu Ile Gly Val Ile Ile Thr Trp
1               5                   10

<210> SEQ ID NO 42
<211> LENGTH: 13
<212> TYPE: PRT
<213> ORGANISM: Artificial Sequence
<220> FEATURE:
<223> OTHER INFORMATION: Synthetic peptide

<400> SEQUENCE: 42

Ser Trp Thr Met Lys Gly Val Ile Ile Thr Trp Ile Gly
1               5                   10

<210> SEQ ID NO 43
<211> LENGTH: 14
<212> TYPE: PRT
<213> ORGANISM: Artificial Sequence
<220> FEATURE:
<223> OTHER INFORMATION: Synthetic peptide

<400> SEQUENCE: 43

Ser Trp Thr Met Lys Ile Gly Val Ile Ile Thr Trp Ile Gly
1               5                   10

<210> SEQ ID NO 44
<211> LENGTH: 15
<212> TYPE: PRT
<213> ORGANISM: Artificial Sequence
<220> FEATURE:
<223> OTHER INFORMATION: Synthetic peptide

<400> SEQUENCE: 44

Pro Gly Phe Thr Met Met Ala Ala Ile Leu Ala Tyr Thr Ile Gly
1               5                   10                  15

<210> SEQ ID NO 45
<211> LENGTH: 14
<212> TYPE: PRT
<213> ORGANISM: Artificial Sequence
<220> FEATURE:
<223> OTHER INFORMATION: Synthetic peptide

<400> SEQUENCE: 45

Pro Gly Phe Thr Met Met Ala Ile Leu Ala Tyr Thr Ile Gly
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Synthetic peptide

<400> SEQUENCE: 46

Pro Gly Phe Thr Met Met Ile Leu Ala Tyr Thr Ile Gly
1               5                   10
```

<210> SEQ ID NO 47
<211> LENGTH: 12
<212> TYPE: PRT
<213> ORGANISM: Artificial Sequence
<220> FEATURE:
<223> OTHER INFORMATION: Synthetic peptide

<400> SEQUENCE: 47

Pro Gly Phe Thr Met Met Leu Ala Tyr Thr Ile Gly
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Synthetic peptide

<400> SEQUENCE: 48

Pro Gly Phe Thr Met Met Ala Tyr Thr Ile Gly
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Synthetic peptide

<400> SEQUENCE: 49

Pro Gly Phe Thr Met Met Tyr Thr Ile Gly
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Synthetic peptide

<400> SEQUENCE: 50

Pro Gly Phe Thr Met Ala Ala Ile Leu Ala Tyr Thr Ile Gly
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Synthetic peptide

<400> SEQUENCE: 51

Pro Gly Phe Thr Ala Ala Ile Leu Ala Tyr Thr Ile Gly
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Synthetic peptide

<400> SEQUENCE: 52

Pro Gly Phe Ala Ala Ile Leu Ala Tyr Thr Ile Gly
1               5                   10

```
<210> SEQ ID NO 53
<211> LENGTH: 11
<212> TYPE: PRT
<213> ORGANISM: Artificial Sequence
<220> FEATURE:
<223> OTHER INFORMATION: Synthetic peptide

<400> SEQUENCE: 53

Pro Gly Ala Ala Ile Leu Ala Tyr Thr Ile Gly
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Synthetic peptide

<400> SEQUENCE: 54

Ser Trp Thr Met Lys Ile Val Ile Ile Thr Trp Ile Gly
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Synthetic peptide

<400> SEQUENCE: 55

Ser Trp Thr Met Lys Ile Leu Ile Thr Trp Ile Gly
1               5                   10

<210> SEQ ID NO 56
<211> LENGTH: 16
<212> TYPE: PRT
<213> ORGANISM: Artificial Sequence
<220> FEATURE:
<223> OTHER INFORMATION: Synthetic peptide

<400> SEQUENCE: 56

Ser Trp Thr Met Lys Ile Leu Ile Pro Val Ile Ile Thr Trp Ile Gly
1               5                   10                  15
```